United States Patent [19]
O'Hara et al.

[11] Patent Number: 5,281,520
[45] Date of Patent: Jan. 25, 1994

[54] METHOD FOR PRODUCING ACYLOXYACYL HYDROLASE

[75] Inventors: Patrick J. O'Hara; Frederick S. Hagen; Francis J. Grant, all of Seattle, Wash.; Robert S. Munford, Dallas, Tex.

[73] Assignees: ZymoGenetics, Inc., Seattle, Wash.; Board of Regents University of Texas System, Austin, Tex.

[21] Appl. No.: 581,342

[22] Filed: Sep. 12, 1990

[51] Int. Cl.$^5$ .............. C12N 15/00; C12N 15/56; C12N 15/80; C12N 15/85
[52] U.S. Cl. .............. 435/69.1; 435/177.3; 435/197; 435/252.3; 435/320.1; 536/23.2; 536/23.1; 935/9; 935/14; 935/28; 935/32; 935/68; 935/70
[58] Field of Search .............. 536/27; 435/69.1-69.9, 435/172.3, 320.1, 252.3, 197

[56] References Cited

U.S. PATENT DOCUMENTS

| | | | |
|---|---|---|---|
| 5,013,652 | 5/1991 | Strausberg et al. | 435/69.2 |
| 5,013,661 | 5/1991 | Munford et al. | 435/197 |
| 5,047,336 | 9/1991 | Cate et al. | 435/69.4 |
| 5,075,227 | 12/1991 | Hagen | 435/172.3 |

OTHER PUBLICATIONS

Munford, R. S., and C. L. Hall, 1989, The Journal of Biological Chemistry, 264(26):15613-15619.
Frohman, M. A., et al., 1988, Proceedings of The National Academy of Sciences, USA, 85:8998-9002.
Belyavsky, A., et al, 1989 Nucleic Acids Research, 17(8):2919-2932.
Mellman, I. S., and J. C. Unkeless, 1980, The Journal of Experimental Medicine, 152: 1048-1069.
Munford and Hall (*Science* 234: 203-205, (1986).
Lee et al. (*Science* 239: 1288-1291, (1988).
Mickel et al. (*J. Biol. Chem.* 264: 12895-12901, (1989).
Lowe et al. (*J. Biol. Chem.* 264: 20042-20046, (1989).

*Primary Examiner*—Robert A. Wax
*Assistant Examiner*—William W. Moore
*Attorney, Agent, or Firm*—Townsend and Townsend

[57] ABSTRACT

Methods are disclosed for producing acyloxyacyl hydrolase. The protein is produced from eukaryotic host cells transformed or transfected with DNA construct(s) containing information necessary to direct the expression of acyloxyacyl hydrolase. The DNA constructs generally include the following operably linked elements: a transcriptional promoter; DNA sequence encoding acyloxyacyl hydrolase, the small subunit of acyloxyacyl hydrolase or the large subunit of acyloxyacyl hydrolase; and a transcriptional terminator. In addition, isolated DNA sequences encoding acyloxyacyl hydrolase and isolated DNA sequences encoding the small or large subunit of acyloxyacyl hydrolase are disclosed.

56 Claims, 19 Drawing Sheets

```
       10         20         30         40         50         60
CCTCCAGCTC TTTGTGTGTG GCTCTCTCAG GGTCCAACAA GAGCAAGCTG TGGGTCTGTG
       70         80         90        100        110        120
AGTGTTTATG TGTGCTTTTA TTCACTTCAC ACTTATTGAA AAGTGTGTAT GTGAGAGGGT
      130        140        150        160        170        180
GGGGTGTGTG TGTCAAAGAG AGTGAGGAAG AGAAGGAGAG AGAGATCAAT TGATTCTGCA
      190        200        210        220        230        240
GCCTCAGCTC CAGCATCCCT CAGTTGGGAG CTTCCAAAGC CGGGTGATCA CTTGGGGTGC
      250            260        269        278        287
ATAGCTCGGA G ATG CAG TCC CCC TGG AAA ATC CTT ACG GTG GCG CCT CTA
             Met Gln Ser Pro Trp Lys Ile Leu Thr Val Ala Pro Leu
     296        305        314        323        332
TCC TTG CTC CTG TCT CTT CAG TCC TTG GCC TCT CCA GCC AAC GAT GAC
Ser Leu Leu Leu Ser Leu Gln Ser Leu Ala Ser Pro Ala Asn Asp Asp
 341            350        359        368        377        386
CAG TCC AGG CCC AGC CTC TCG AAT GGG CAC ACC TGT GTA GGG TGT GTG
Gln Ser Arg Pro Ser Leu Ser Asn Gly His Thr Cys Val Gly Cys Val
         395        404        413        422        431
CTG GTG GTG TCT GTA ATA GAA CAG CTT GCT CAA GTT CAC AAC TCG ACG
Leu Val Val Ser Val Ile Glu Gln Leu Ala Gln Val His Asn Ser Thr
     440        449        458        467        476
GTC CAG GCC TCG ATG GAG AGA CTG TGC AGC TAC CTG CCT GAA AAA CTG
Val Gln Ala Ser Met Glu Arg Leu Cys Ser Tyr Leu Pro Glu Lys Leu
 485        494        503        512        521        530
TTC TTG AAA ACC ACC TGC TAT TTA GTC ATT GAC AAG TTT GGA TCA GAC
Phe Leu Lys Thr Thr Cys Tyr Leu Val Ile Asp Lys Phe Gly Ser Asp
         539        548        557        566        575
ATC ATA AAA CTG CTT AGC GCA GAT ATG AAT GCT GAT GTG GTA TGT CAC
Ile Ile Lys Leu Leu Ser Ala Asp Met Asn Ala Asp Val Val Cys His
     584        593        602        611        620
ACT CTG GAG TTT TGT AGA CAG AAC ACT GGC CAA CCA TTG TGT CAT CTC
Thr Leu Glu Phe Cys Arg Gln Asn Thr Gly Gln Pro Leu Cys His Leu
 629        638        647        656        665        674
TAC CCT CTT CCC AAG GAG ACA TGG AAA TTT ACA CTA CAG AAG GCA AGA
Tyr Pro Leu Pro Lys Glu Thr Trp Lys Phe Thr Leu Gln Lys Ala Arg
         683        692        761        710        719
CAA ATT ATC AAG AAG TCC CCG ATT CTG AAA TAT TCT AGA AGT GGT TCT
Gln Ile Ile Lys Lys Ser Pro Ile Leu Lys Tyr Ser Arg Ser Gly Ser
     728        737        746        755        764
GAC ATT TGT TCA CTC CCG GTT TTG GCC AAG ATC TGC CAG AAA ATT AAA
Asp Ile Cys Ser Leu Pro Val Leu Ala Lys Ile Cys Gln Lys Ile Lys
```

*FIG. IA.*

```
 773              782              791              800              809              818
 TTA GCT ATG GAA CAG TCT GTG CCA TTC AAA GAT GTG GAT TCA GAC AAA
 Leu Ala Met Glu Gln Ser Val Pro Phe Lys Asp Val Asp Ser Asp Lys 827              836              845              854              863
 TAC AGC GTT CTC CCA ACA CTG CGG GGC TAT CAC TGG CGG GGG AGA GAC
 Tyr Ser Val Leu Pro Thr Leu Arg Gly Tyr His Trp Arg Gly Arg Asp 872              881              890              899              908
 TGT AAT GAC AGC GAC GAG TCA GTG TAC CCA GGT AGA AGG CCG AAC AAC
 Cys Asn Asp Ser Asp Glu Ser Val Tyr Pro Gly Arg Arg Pro Asn Asn 917              926              935              944              953              962
 TGG GAT GTC CAT CAG GAT TCA AAC TGT AAT GGC ATT TGG GGT GTC GAT
 Trp Asp Val His Gln Asp Ser Asn Cys Asn Gly Ile Trp Gly Val Asp 971              980              989              998              1007
 CCA AAA GAT GGA GTT CCA TAT GAG AAG AAA TTC TGT GAA GGT TCA CAG
 Pro Lys Asp Gly Val Pro Tyr Glu Lys Lys Phe Cys Glu Gly Ser Gln 1016             1025             1034             1043             1052
 CCC AGG GGA ATC ATT TTG CTG GGA GAC TCA GCT GGG GCT CAT TTT CAC
 Pro Arg Gly Ile Ile Leu Leu Gly Asp Ser Ala Gly Ala His Phe His 1064     1070             1079             1088             1097     1106
 ATC TCT CCT GAA TGG ATC ACA GCG TCG CAG ATG TCT TTG AAC TCT TTC
 Ile Ser Pro Glu Trp Ile Thr Ala Ser Gln Met Ser Leu Asn Ser Phe 1115             1124             1133             1142             1151
 ATC AAT CTA CCA ACA GCC CTT ACC AAC GAG CTT GAC TGG CCC CAA CTC
 Ile Asn Leu Pro Thr Ala Leu Thr Asn Glu Leu Asp Trp Pro Gln Leu 1160             1169             1178             1187             1196
 TCT GGT GCT ACA GGA TTT CTG GAC TCC ACT GTT GGA ATT AAA GAA AAA
 Ser Gly Ala Thr Gly Phe Leu Asp Ser Thr Val Gly Ile Lys Glu Lys 1206        1214             1223             1232             1241             1250
 TCT ATT TAC CTT CGC TTA TGG AAA AGA AAC CAC TGT AAT CAC AGG GAC
 Ser Ile Tyr Leu Arg Leu Trp Lys Arg Asn His Cys Asn His Arg Asp 1259             1268             1277             1286             1295
 TAC CAG AAT ATT TCA AGA AAT GGT GCA TCT TCC CGA AAC CTG AAG AAA
 Tyr Gln Asn Ile Ser Arg Asn Gly Ala Ser Ser Arg Asn Leu Lys Lys 1304             1313             1322             1331             1340
 TTT ATA GAA AGC TTG TCT AGA AGC AAG GTG TTG GAC TAT CCC GCC ATC
 Phe Ile Glu Ser Leu Ser Arg Ser Lys Val Leu Asp Tyr Pro Ala Ile 1350             1358             1367             1376             1385             1394
 GTT ATA TAT GCC ATG ATT GGA AAT GAT GTC TGC AGT GGG AAG AGT GAC
 Val Ile Tyr Ala Met Ile Gly Asn Asp Val Cys Ser Gly Lys Ser Asp 1403             1412             1421             1430             1439
 CCA GTC CCA GCC ATG ACC ACT CCT GAG AAA CTC TAC TCC AAC GTC ATG
 Pro Val Pro Ala Met Thr Thr Pro Glu Lys Leu Tyr Ser Asn Val Met
```

*FIG. 1B.*

```
         1448         1457         1466         1475         1484
CAG ACT CTG AAG CAT CTA AAT TCC CAC CTG CCC AAT GGC AGC CAT GTT
Gln Thr Leu Lys His Leu Asn Ser His Leu Pro Asn Gly Ser His Val 1494         1502         1511         1520         1529         1538
ATT TTG TAT GGC TTA CCA GAT GGA ACC TTT CTC TGG GAT AAT TTG CAC
Ile Leu Tyr Gly Leu Pro Asp Gly Thr Phe Leu Trp Asp Asn Leu His 1547         1556         1565         1574         1593
AAC AGA TAT CAT CCT CTC GGC CAG CTA AAT AAA GAC ATG ACC TAT GCG
Asn Arg Tyr His Pro Leu Gly Gln Leu Asn Lys Asp Met Thr Tyr Ala 1592         1601         1610         1619         1628
CAG TTG TAC TCC TTC CTG AAC TGC TTC CAG GTC AGC CCC TGC CAC GGC
Gln Leu Tyr Ser Phe Leu Asn Cys Phe Gln Val Ser Pro Cys His Gly 1638         1646         1655         1664         1673         1682
TGG ATG TCT TCC AAC AAG ACG TTG CGG ACT CTC ACT TCA GAG AGA GCA
Trp Met Ser Ser Asn Lys Thr Leu Arg Thr Leu Thr Ser Glu Arg Ala 1691         1700         1709         1718         1727
GAG CAA CTC TCC AAC ACA CTG AAA AAA ATT GCA GCC AGT GAG AAA TTT
Glu Gln Leu Ser Asn Thr Leu Lys Lys Ile Ala Ala Ser Glu Lys Phe 1736         1745         1754         1763         1772
ACA AAC TTC AAT CTT TTC TAC ATG GAT TTT GCC TTC CAT GAA ATC ATA
Thr Asn Phe Asn Leu Phe Tyr Met Asp Phe Ala Phe His Glu Ile Ile 1782         1790         1799         1808         1817         1826
CAG GAG TGG CAG AAG AGA GGC GGA CAG CCC TGG CAG CTC ATC GAG CCC
Gln Glu Trp Gln Lys Arg Gly Gly Gln Pro Trp Gln Leu Ile Glu Pro 1835         1844         1853         1862         1871
GTG GAT GGA TTC CAC CCC AAC GAG GTG GCT TTG CTG TTG TTG GCG GAT
Val Asp Gly Phe His Pro Asn Glu Val Ala Leu Leu Leu Leu Ala Asp 1880         1889         1898         1907         1916
CAT TTC TGG AAA AAG GTG CAG CTC CAG TGG CCC CAA ATC CTG GGA AAG
His Phe Trp Lys Lys Val Gln Leu Gln Trp Pro Gln Ile Leu Gly Lys 1926         1934         1943         1952         1961         1970
GAG AAT CCG TTC AAC CCC CAG ATT AAA CAG GTG TTT GGA GAC CAA GGC
Glu Asn Pro Phe Asn Pro Gln Ile Lys Gln Val Phe Gly Asp Gln Gly 1979         1989         1999         2009         2019
GGG CAC TGAGCCTCTC AGGAGCATGC ACCCCTGGGG AGCACAGGGA GGCAGAGGCT
Gly His 2020         2039         2049         2059         2069         2079
TGGGTAAACT CATTCCACAA ACCCTATGGG GGCTGCCACG TCACAGGCCC AAAGGACTCT 2090         2099         2109         2119         2129         2139
TCTTCAGCAG CATCTTTGCA AAATGTCTTT CTCTCAATGA AGAGCATATC TGGACGACTG 2150         2159
TGCAATGCTG TGTGCTC
```

FIG. 1C.

```
        10         20         30         40         50         60
CCTCCAGCTC TTTGTGTGTG GCTCTCTCAG GGTCCAACAA GAGCAAGCTG TGGGTCTGTG 70         80         90        100        110        120
AGTGTTTATG TGTGCTTTTA TTCACTTCAC ACTTATTGAA AAGTGTGTAT GTGAGAGGGT 130        140        150        160        170        180
GGGGTGTGTG TGTCAAAGAG AGTGAGGAAG AGAAGGAGAG AGAGATCAAT TGATTCTGCA 190        200        210        220        230        240
GCCTCAGCTC CAGCATCCCT CAGTTGGGAG CTTCCAAAGC CGGGTGATCA CTTGGGGTGC 250              260        269        278        287
ATAGCTCGGA G ATG CAG TCC CCC TGG AAA ATC CTT ACG GTG GCG CCT CTA
             Met Gln Ser Pro Trp Lys Ile Leu Thr Val Ala Pro Leu
```

```
296         305         314         323         332
TTC TTG CTC CTG TCT CTT CAG TCC TCG GCC TCT CCA GCC AAC GAT GAC
Phe Leu Leu Leu Ser Leu Gln Ser Ser Ala Ser Pro Ala Asn Asp Asp 341         350         359         368         377         386
CAG TCC AGG CCC AGC CTC TCG AAT GGG CAC ACC TGT GTA GGG TGT GTG
Gln Ser Arg Pro Ser Leu Ser Asn Gly His Thr Cys Val Gly Cys Val 395         404         413         422         431
CTG GTG GTG TCT GTA ATA GAA CAG CTT GCT CAA GTT CAC AAC TCG ACG
Leu Val Val Ser Val Ile Glu Gln Leu Ala Gln Val His Asn Ser Thr 440         449         458         467         476
GTC CAG GCC TCG ATG GAG AGA CTG TGC AGC TAC CTG CCT GAA AAA CTG
Val Gln Ala Ser Met Glu Arg Leu Cys Ser Tyr Leu Pro Glu Lys Leu 485         494         503         512         521         530
TTC TTG AAA ACC ACC TGC TAT TTA GTC ATT GAC AAG TTT GGA TCA GAC
Phe Leu Lys Thr Thr Cys Tyr Leu Val Ile Asp Lys Phe Gly Ser Asp 539         548         557         566         575
ATC ATA AAA CTG CTT AGC GCA GAT ATG AAT GCT GAT GTG GTA TGT CAC
Ile Ile Lys Leu Leu Ser Ala Asp Met Asn Ala Asp Val Val Cys His 584         593         602         611         620
ACT CTG GAG TTT TGT AAA CAG AGC ACT GGC CAA CCA TTG TGT CAT CTC
Thr Leu Glu Phe Cys Lys Gln Ser Thr Gly Gln Pro Leu Cys His Leu 629         638         647         656         665         674
TAC CCT CTT CCC AAG GAG ACA TGG AAA TTT ACA CTA CAG AAG GCA AGA
Tyr Pro Leu Pro Lys Glu Thr Trp Lys Phe Thr Leu Gln Lys Ala Arg 683         692         761         710         719
CAA ATT GTC AAG AAG TCC CCG ATT CTG AAA TAT TCT AGA AGT GGT TCT
Gln Ile Val Lys Lys Ser Pro Ile Leu Lys Tyr Ser Arg Ser Gly Ser 728         737         746         755         764
GAC ATT TGT TCA CTC CCG GTT TTG GCC AAG ATC TGC CAG AAA ATT AAA
Asp Ile Cys Ser Leu Pro Val Leu Ala Lys Ile Cys Gln Lys Ile Lys
```

FIG. 2A.

```
 773           782           791           800           809           818
TTA GCT ATG GAA CAG TCT GTG CCA TTC AAA GAT GTG GAT TCA GAC AAA
Leu Ala Met Glu Gln Ser Val Pro Phe Lys Asp Val Asp Ser Asp Lys 827           836           845           854           863
TAC AGC GTT TTC CCA ACA CTG CGG GGC TAT CAC TGG CGG GGG AGA GAC
Tyr Ser Val Phe Pro Thr Leu Arg Gly Tyr His Trp Arg Gly Arg Asp 872           881           890           899           908
TGT AAT GAC AGC GAC GAG TCA GTG TAC CCA GGT AGA AGG CCG AAC AAC
Cys Asn Asp Ser Asp Glu Ser Val Tyr Pro Gly Arg Arg Pro Asn Asn 917           926           935           944           953           962
TGG GAT GTC CAT CAG GAT TCA AAC TGT AAT GGC ATT TGG GGT GTC GAT
Trp Asp Val His Gln Asp Ser Asn Cys Asn Gly Ile Trp Gly Val Asp 971           980           989           998          1007
CCA AAA GAT GGA GTT CCA TAT GAG AAG AAA TTC TGT GAA GGT TCA CAG
Pro Lys Asp Gly Val Pro Tyr Glu Lys Lys Phe Cys Glu Gly Ser Gln 1016          1025          1034          1043          1052
CCC AGG GGA ATC ATT TTG CTG GGA GAC TCA GCT GGG GCT CAT TTT CAC
Pro Arg Gly Ile Ile Leu Leu Gly Asp Ser Ala Gly Ala His Phe His 1064      1070          1079          1088          1097          1106
ATC TCT CCT GAA TGG ATC ACA GCG TCG CAG ATG TCT TTG AAC TCT TTC
Ile Ser Pro Glu Trp Ile Thr Ala Ser Gln Met Ser Leu Asn Ser Phe 1115          1124          1133          1142          1151
ATC AAT CTA CCA ACA GCC CTT ACC AAC GAG CTT GAC TGG CCC CAA CTC
Ile Asn Leu Pro Thr Ala Leu Thr Asn Glu Leu Asp Trp Pro Gln Leu 1160          1169          1178          1187          1196
TCT GGT GCT ACA GGA TTT CTG GAC TCC ACT GTT GGA ATT AAA GAA AAA
Ser Gly Ala Thr Gly Phe Leu Asp Ser Thr Val Gly Ile Lys Glu Lys 1206       1214          1223          1232          1241          1250
TCT ATT TAC CTT CGC TTA TGG AAA AGA AAC CAC TGT AAT CAC AGG GAC
Ser Ile Tyr Leu Arg Leu Trp Lys Arg Asn His Cys Asn His Arg Asp 1259          1268          1277          1286          1295
TAC CAG AAT ATT TCA AGA AAT GGT GCA TCT TCC CGA AAC CTG AAG AAA
Tyr Gln Asn Ile Ser Arg Asn Gly Ala Ser Ser Arg Asn Leu Lys Lys 1304          1313          1322          1331          1340
TTT ATA GAA AGC TTG TCT AGA AAC AAG GTG TTG GAC TAT CCC GCC ATC
Phe Ile Glu Ser Leu Ser Arg Asn Lys Val Leu Asp Tyr Pro Ala Ile 1350      1358          1367          1376          1385          1394
GTT ATA TAT GCC ATG ATT GGA AAT GAT GTC TGC AGT GGG AAG AGT GAC
Val Ile Tyr Ala Met Ile Gly Asn Asp Val Cys Ser Gly Lys Ser Asp 1403          1412          1421          1430          1439
CCA GTC CCA GCC ATG ACC ACT CCT GAG AAA CTC TAC TCC AAC GTC ATG
Pro Val Pro Ala Met Thr Thr Pro Glu Lys Leu Tyr Ser Asn Val Met
```

*FIG. 2B.*

```
      1448         1457        1466         1475        1484
CGG ACT CTG AAG CAT CTA AAT TCC CAC CTG CCC AAT GGC AGC CAT GTT
Arg Thr Leu Lys His Leu Asn Ser His Leu Pro Asn Gly Ser His Val 1494        1502        1511        1520        1529        1538
ATT TTG TAT GGC TCA CCA GAT GGA ACC TTT CTC TGG GAT AAT TTG CAC
Ile Leu Tyr Gly Ser Pro Asp Gly Thr Phe Leu Trp Asp Asn Leu His 1547        1556        1565        1574        1593
AAC AGA TAT CAT CCT CTC GGC CAG CTA AAT AAA GAC ATG ACC TAT GCG
Asn Arg Tyr His Pro Leu Gly Gln Leu Asn Lys Asp Met Thr Tyr Ala 1592        1601        1610        1619        1628
CAG TTG TAC TCC TTC CTG AAC TGC CTC CAG GTC AGC CCC TGC CAC GGC
Gln Leu Tyr Ser Phe Leu Asn Cys Leu Gln Val Ser Pro Cys His Gly 1638        1646        1655        1664        1673        1682
TGG ATG TCT TCC AAC AAG ACG TTG CGG ACT CTC ACT TCA GAG AGA GCA
Trp Met Ser Ser Asn Lys Thr Leu Arg Thr Leu Thr Ser Glu Arg Ala 1691        1700        1709        1718        1727
GAG CAA CTC TCC AAC ACA CTG AAA AAA ATT GCA GCC AGT GAG AAA TTT
Glu Gln Leu Ser Asn Thr Leu Lys Lys Ile Ala Ala Ser Glu Lys Phe 1736        1745        1754        1763        1772
ACA AAC TTC AAT CTT TTC TAC ATG GAT TTT GCC TTC CAT GAA ATC ATA
Thr Asn Phe Asn Leu Phe Tyr Met Asp Phe Ala Phe His Glu Ile Ile 1782        1790        1799        1808        1817        1826
CAG GAG TGG CAG AAG AGA GGC GGA CAG CCC TGG CAG CTC ATC GAG CCC
Gln Glu Trp Gln Lys Arg Gly Gly Gln Pro Trp Gln Leu Ile Glu Pro 1835        1844        1853        1862        1871
GTG GAT GGA TTC CAC CCC AAC GAG GTG GCT TTG CTG TTG TTG GCG GAT
Val Asp Gly Phe His Pro Asn Glu Val Ala Leu Leu Leu Leu Ala Asp 1880        1889        1898        1907        1916
CAT TTC TGG AAA AAG GTG CAG CTC CAG TGG CCC CAA ATC CTG GGA AAG
His Phe Trp Lys Lys Val Gln Leu Gln Trp Pro Gln Ile Leu Gly Lys 1926    1934        1943        1952        1961        1970
GAG AAT CCG TTC AAC CCC CAG ATT AAA CAG GTG TTT GGA GAC CAA GGC
Glu Asn Pro Phe Asn Pro Gln Ile Lys Gln Val Phe Gly Asp Gln Gly 1979      1989       1999       2009       2019
GGG CAC TGAGCCTCTC AGGAGCATGC ACCCCTGGGG AGCACAGGGA GGCAGAGGCT
Gly His 2020       2039       2049       2059       2069       2079
TGGGTAAACT CATTCCACAA ACCCTATGGG GGCTGCCACG TCACAGGCCC AAAGGACTCT 2090       2099       2109       2119       2129       2139
TCTTCAGCAG CATCTTTGCA AAATGTCTTT CTCTCAATGA AGAGCATATC TGGACGACTG 2150       2159
TGCAATGCTG TGTGCTC
```

FIG. 2C.

```
         10          20         30         40         50         60
GAATTCGCGG CCGCAGAACC GCACACCACA GACTCCCTCC AGCTCTTTGT GTGTGGCTCT 70          80         90        100        110        120
CTCAGGGTCC AACAAGAGCA AGCTGTGGGT CTGTGAGTGT TTATGTGTGC TTTTATTCAC 130         140        150        160        170        180
TTCACACTTA TTGAAAAGTG TGTATGTGAG AGGGTGGGGT GTGTGTGTCA AAGAGAGTGA 190         200        210        220        230        240
GGAAGAGAAG GAGAGAGAGA TCAATTGATT CTGCAGCCTC AGCTCCAGCA TCCCTCAGTT 250         260        270        280        289
GGGAGCTTCC AAAGCCGGGT GATCACTTGG GGTGCATAGC TCGGAG ATG CAG TCC
                                                    Met Gln Ser 298         307         316         325         334         343
CCC TGG AAA ATC CTT ACG GTG GCG CCT CTA TTC TTG CTC CTG TCT CTT
Pro Trp Lys Ile Leu Thr Val Ala Pro Leu Phe Leu Leu Leu Ser Leu 352         361         370         379         388
CAG TCC TCG GCC TCT CCA GCC AAC GAT GAC CAG TCC AGG CCC AGC CTC
Gln Ser Ser Ala Ser Pro Ala Asn Asp Asp Gln Ser Arg Pro Ser Leu 397         406         415         424         433
TCG AAT GGG CAC ACC TGT GTA GGG TGT GTG CTG GTG GTG TCT GTA ATA
Ser Asn Gly His Thr Cys Val Gly Cys Val Leu Val Val Ser Val Ile 442         451         460         469         478         487
GAA CAG CTT GCT CAA GTT CAC AAC TCG ACG GTC CAG GCC TCG ATG GAG
Glu Gln Leu Ala Gln Val His Asn Ser Thr Val Gln Ala Ser Met Glu 496         505         514         523         532
AGA CTG TGC AGC TAC CTG CCT GAA AAA CTG TTC TTG AAA ACC ACC TGC
Arg Leu Cys Ser Tyr Leu Pro Glu Lys Leu Phe Leu Lys Thr Thr Cys 541         550         559         568         577
TAT TTA GTC ATT GAC AAG TTT GGA TCA GAC ATC ATA AAA CTG CTT AGC
Tyr Leu Val Ile Asp Lys Phe Gly Ser Asp Ile Ile Lys Leu Leu Ser 586         595         604         613         622         631
GCA GAT ATG AAT GCT GAT GTG GTA TGT CAC ACT CTG GAG TTT TGT AAA
Ala Asp Met Asn Ala Asp Val Val Cys His Thr Leu Glu Phe Cys Lys 640         649         658         667         676
CAG AAC ACT GGC CAA CCA TTG TGT CAT CTC TAC CCT CTT CCC AAG GAG
Gln Asn Thr Gly Gln Pro Leu Cys His Leu Tyr Pro Leu Pro Lys Glu 685         694         703         712         721
ACA TGG AAA TTT ACA CTA CAG AAG GCA AGA CAA ATT GTC AAG AAG TCC
Thr Trp Lys Phe Thr Leu Gln Lys Ala Arg Gln Ile Val Lys Lys Ser 730         739         748         757         766         775
CCG ATT CTG AAA TAT TCT AGA AGT GGT TCT GAC ATT TGT TCA CTC CCG
Pro Ile Leu Lys Tyr Ser Arg Ser Gly Ser Asp Ile Cys Ser Leu Pro
```

*FIG. 3A.*

```
          784           793           802           811           820
GTT TTG GCC AAG ATC TGC CAG AAA ATT AAA TTA GCT ATG GAA CAG TCT
Val Leu Ala Lys Ile Cys Gln Lys Ile Lys Leu Ala Met Glu Gln Ser 829           838           847           856           865
GTG CCA TTC AAA GAT GTG GAT TCA GAC AAA TAC AGC GTT TTC CCA ACA
Val Pro Phe Lys Asp Val Asp Ser Asp Lys Tyr Ser Val Phe Pro Thr 874           883           892           901           910           919
CTG CGG GGC TAT CAC TGG CGG GGG AGA GAC TGT AAT GAC AGC GAC GAG
Leu Arg Gly Tyr His Trp Arg Gly Arg Asp Cys Asn Asp Ser Asp Glu 928           937           946           955           964
TCA GTG TAC CCA GGT AGA AGG CCG AAC AAC TGG GAT GTC CAT CAG GAT
Ser Val Tyr Pro Gly Arg Arg Pro Asn Asn Trp Asp Val His Gln Asp 973           982           991          1000          1009
TCA AAC TGT AAT GGC ATT TGG GGT GTC GAT CCA AAA GAT GGA GTT CCA
Ser Asn Cys Asn Gly Ile Trp Gly Val Asp Pro Lys Asp Gly Val Pro 1019       1027          1036          1045          1054          1063
TAT GAG AAG AAA TTC TGT GAA GGT TCA CAG CCC AGG GGA ATC ATT TTG
Tyr Glu Lys Lys Phe Cys Glu Gly Ser Gln Pro Arg Gly Ile Ile Leu 1072          1081          1090          1099          1108
CTG GGA GAC TCA GCT GGG GCT CAT TTT CAC ATC TCT CCT GAA TGG ATC
Leu Gly Asp Ser Ala Gly Ala His Phe His Ile Ser Pro Glu Trp Ile 1117          1126          1135          1144          1153
ACA GCG TCG CAG ATG TCT TTG AAC TCT TTC ATC AAT CTA CCA ACA GCC
Thr Ala Ser Gln Met Ser Leu Asn Ser Phe Ile Asn Leu Pro Thr Ala 1163      1171          1180          1189          1198         1207
CTT ACC AAC GAG CTT GAC TGG CCC CAA CTC TCT GGT GCT ACA GGA TTT
Leu Thr Asn Glu Leu Asp Trp Pro Gln Leu Ser Gly Ala Thr Gly Phe 1216          1225          1234          1243          1252
CTG GAC TCC ACT GTT GGA ATT AAA GAA AAA TCT ATT TAC CTT CGC TTA
Leu Asp Ser Thr Val Gly Ile Lys Glu Lys Ser Ile Tyr Leu Arg Leu 1261          1270          1279          1288          1297
TGG AAA AGA AAC CAC TGT AAT CAC AGG GAC TAC CAG AAT ATT TCA AGA
Trp Lys Arg Asn His Cys Asn His Arg Asp Tyr Gln Asn Ile Ser Arg 1307       1315          1324          1333          1342         1351
AAT GGT GCA TCT TCC CGA AAC CTG AAG AAA TTT ATA GAA AGC TTG TCT
Asn Gly Ala Ser Ser Arg Asn Leu Lys Lys Phe Ile Glu Ser Leu Ser 1360          1369          1378          1387          1396
AGA AAC AAG GTG TTG GAC TAT CCC GCC ATC GTT ATA TAT GCC ATG ATT
Arg Asn Lys Val Leu Asp Tyr Pro Ala Ile Val Ile Tyr Ala Met Ile 1405          1414          1423          1432          1441
GGA AAT GAT GTC TGC AGT GGG AAG AGT GAC CCA GTC CCA GCC ATG ACC
Gly Asn Asp Val Cys Ser Gly Lys Ser Asp Pro Val Pro Ala Met Thr
```

FIG. 3B.

```
     1451           1459           1468           1477           1486           1495
ACT CCT GAG AAA CTC TAC TCC AAC GTC ATG CAG ACT CTG AAG CAT CTA
Thr Pro Glu Lys Leu Tyr Ser Asn Val Met Gln Thr Leu Lys His Leu 1504           1513           1522           1531           1540
AAT TCC CAC CTG CCC AAT GGC AGC CAT GTT ATT TTG TAT GGC TTA CCA
Asn Ser His Leu Pro Asn Gly Ser His Val Ile Leu Tyr Gly Leu Pro 1549           1558           1567           1576           1585
GAT GGA ACC TTT CTC TGG GAT AAT TTG CAC AAC AGA TAT CAT CCT CTC
Asp Gly Thr Phe Leu Trp Asp Asn Leu His Asn Arg Tyr His Pro Leu 1595       1603           1612           1621           1630           1639
GGC CAG CTA AAT AAA GAC ATG ACC TAT GCG CAG TTG TAC TCC TTC CTG
Gly Gln Leu Asn Lys Asp Met Thr Tyr Ala Gln Leu Tyr Ser Phe Leu 1648           1657           1666           1675           1684
AAC TGC CTC CAG GTC AGC CCC TGC CAC GGC TGG ATG TCT TCC AAC AAG
Asn Cys Leu Gln Val Ser Pro Cys His Gly Trp Met Ser Ser Asn Lys 1693           1702           1711           1720           1729
ACG TTG CGG ACT CTC ACT TCA GAG AGA GCA GAG CAA CTC TCC AAC ACA
Thr Leu Arg Thr Leu Thr Ser Glu Arg Ala Glu Gln Leu Ser Asn Thr 1739           1747           1756           1765           1774           1783
CTG AAA AAA ATT GCA GCC AGT GAG AAA TTT ACA AAC TTC AAT CTT TTC
Leu Lys Lys Ile Ala Ala Ser Glu Lys Phe Thr Asn Phe Asn Leu Phe 1792           1801           1810           1819           1828
TAC ATG GAT TTT GCC TTC CAT GAA ATC ATA CAG GAG TGG CAG AAG AGA
Tyr Met Asp Phe Ala Phe His Glu Ile Ile Gln Glu Trp Gln Lys Arg 1837           1846           1855           1864           1873
GGC GGA CAG CCC TGG CAG CTC ATC GAG CCC GTG GAT GGA TTC CAC CCC
Gly Gly Gln Pro Trp Gln Leu Ile Glu Pro Val Asp Gly Phe His Pro 1883       1891           1900           1909           1918           1927
AAC GAG GTG GCT TTG CTG TTG TTG GCG GAT CAT TTC TGG AAA AAG GTG
Asn Glu Val Ala Leu Leu Leu Leu Ala Asp His Phe Trp Lys Lys Val 1936           1945           1954           1963           1972
CAG CTC CAG TGG CCC CAA ATC CTG GGA AAG GAG AAT CCG TTC AAC CCC
Gln Leu Gln Trp Pro Gln Ile Leu Gly Lys Glu Asn Pro Phe Asn Pro 1981           1990           1999           2008     2014
CAG ATT AAA CAG GTG TTT GGA GAC CAA GGC GGG CAC TGA GCCTCTC
Gln Ile Lys Gln Val Phe Gly Asp Gln Gly Gly His 2024       2034       2044       2054       2064       2074
AGGAGCATGC ACCCCTGGGG AGCACAGGGA GGCAGAGGCT TGGGTAAACT CATTCCACAA 2084       2094       2104       2114       2124       2134
ACCCTATGGG GGCTGCCACG TCACAGGCCC AAAGGACTCT TCTTCAGCAG CATCTTTGCA 2144       2154       2164       2174       2184       2194
AAATGTCTTT CTCTCAATGA AGAGCATATC TGGACGACTG TGCAATGCTG TGTGCTCCG
```

*FIG. 3C.*

```
       2204       2214       2224       2234       2244       2254
GGATCAGTAA CCCTTCCGCT GTTCCTGAAA TAACCTTTCA TAAAGTGCTT TGGGTGCCAT
       2264       2274       2284
TCCAAAAAAA AAAAAAAAAA AAAAAAAAAA
```

*FIG. 3D.*

```
              10         20                29            38            47
GAATTCGTCG ACCACC ATG CAG TCC CCC TGG AAA ATC CTT ACG GTG GCG
                  Met Gln Ser Pro Trp Lys Ile Leu Thr Val Ala 56          65          74          83          92
CCT CTA TTC TTG CTC CTG TCT CTT CAG TCC TCG GCC TCT CCA GCC AAC
Pro Leu Phe Leu Leu Leu Ser Leu Gln Ser Ser Ala Ser Pro Ala Asn 101         110         119↓        128         137         146
GAT GAC CAG TCC AGG CCC AGC CTC TCG AAT GGG CAC ACC TGT GTA GGG
Asp Asp Gln Ser Arg Pro Ser Leu Ser Asn Gly His Thr Cys Val Gly 155         164         173         182         191
TGT GTG CTG GTG GTG TCT GTA ATA GAA CAG CTT GCT CAA GTT CAC AAC
Cys Val Leu Val Val Ser Val Ile Glu Gln Leu Ala Gln Val His Asn 200         209         218         227         236
TCG ACG GTC CAG GCC TCG ATG GAG AGA CTG TGC AGC TAC CTG CCT GAA
Ser Thr Val Gln Ala Ser Met Glu Arg Leu Cys Ser Tyr Leu Pro Glu 245         254         263         272         281         290
AAA CTG TTC TTG AAA ACC ACC TGC TAT TTA GTC ATT GAC AAG TTT GGA
Lys Leu Phe Leu Lys Thr Thr Cys Tyr Leu Val Ile Asp Lys Phe Gly 299         208         317         326         335
TCA GAC ATC ATA AAA CTG CTT AGC GCA GAT ATG AAT GCT GAT GTG GTA
Ser Asp Ile Ile Lys Leu Leu Ser Ala Asp Met Asn Ala Asp Val Val 344         353         362         371         380
TGT CAC ACT CTC GAG TTT TGT AAA CAG AAC ACT GGC CAA CCA TTG TGT
Cys His Thr Leu Glu Phe Cys Lys Gln Asn Thr Gly Gln Pro Leu Cys 389         398         407         416         425         434
CAT CTC TAC CCT CTT CCC AAG GAG ACA TGG AAA TTT ACA CTA CAG AAG
His Leu Tyr Pro Leu Pro Lys Glu Thr Trp Lys Phe Thr Leu Gln Lys 443         452         461         470         479
GCA AGA CAA ATT GTC AAG AAG TCC CCG ATT CTG AAA TAT TCT AGA AGT
Ala Arg Gln Ile Val Lys Lys Ser Pro Ile Leu Lys Tyr Ser Arg Ser

↓488         497         506         515         524
GGT TCT GAC ATT TGT TCA CTC CCG GTT TTG GCC AAG ATC TGC CAG AAA
Gly Ser Asp Ile Cys Ser Leu Pro Val Leu Ala Lys Ile Cys Gln Lys 533         542         551         560         569         578
ATT AAA TTA GCT ATG GAA CAG TCT GTG CCA TTC AAA GAT GTG GAT TCA
Ile Lys Leu Ala Met Glu Gln Ser Val Pro Phe Lys Asp Val Asp Ser 587         596         605         614         623
GAC AAA TAC AGC GTT TTC CCA ACA CTG CGG GGC TAT CAC TGG CGG GGG
Asp Lys Tyr Ser Val Phe Pro Thr Leu Arg Gly Tyr His Trp Arg Gly 632         641         650         659         668
AGA GAC TGT AAT GAC AGC GAC GAG TCA GTG TAC CCA GGT AGA AGG CCG
Arg Asp Cys Asn Asp Ser Asp Glu Ser Val Tyr Pro Gly Arg Arg Pro
```

*FIG. 4A.*

```
677              686              695              704              713              722
AAC AAC TGG GAT GTC CAT CAG GAT TCA AAC TGT AAT GGC ATT TGG GGT
Asn Asn Trp Asp Val His Gln Asp Ser Asn Cys Asn Gly Ile Trp Gly 731              740              747              758              767
GTC GAT CCA AAA GAT GGA GTT CCA TAT GAG AAG AAA TTC TGT GAA GGT
Val Asp Pro Lys Asp Gly Val Pro Tyr Glu Lys Lys Phe Cys Glu Gly 776              785              794              803              812
TCA CAG CCC AGG GGA ATC ATT TTG CTG GGA GAC TCA GCT GGG GCT CAT
Ser Gln Pro Arg Gly Ile Ile Leu Leu Gly Asp Ser Ala Gly Ala His 821              830              839              848              857              866
TTT CAC ATC TCT CCT GAA TGG ATC ACA GCG TCG CAG ATG TCT TTG AAC
Phe His Ile Ser Pro Glu Trp Ile Thr Ala Ser Gln Met Ser Leu Asn 875              884              893              902              911
TCT TTC ATC AAT CTA CCA ACA GCC CTT ACC AAC GAG CTT GAC TGG CCC
Ser Phe Ile Asn Leu Pro Thr Ala Leu Thr Asn Glu Leu Asp Trp Pro 920              929              938              947              956
CAA CTC TCT GGT GCT ACA GGA TTT CTG GAC TCC ACT GTT GGA ATT AAA
Gln Leu Ser Gly Ala Thr Gly Phe Leu Asp Ser Thr Val Gly Ile Lys 965              974              983              992              1001         1010
GAA AAA TCT ATT TAC CTT CGC TTA TGG AAA AGA AAC CAC TGT AAT CAC
Glu Lys Ser Ile Tyr Leu Arg Leu Trp Lys Arg Asn His Cys Asn His 1019             1028             1037             1046             1055
AGG GAC TAC CAG AAT ATT TCA AGA AAT GGT GCA TCT TCC CGA AAC CTG
Arg Asp Tyr Gln Asn Ile Ser Arg Asn Gly Ala Ser Ser Arg Asn Leu 1064             1073             1082             1091             1100
AAG AAA TTT ATA GAA AGC TTG TCT AGA AAC AAG GTG TTG GAC TAT CCC
Lys Lys Phe Ile Glu Ser Leu Ser Arg Asn Lys Val Leu Asp Tyr Pro 1100         1118             1127             1136             1145             1154
GCC ATC GTT ATA TAT GCC ATG ATT GGA AAT GAT GTC TGC AGT GGG AAG
Ala Ile Val Ile Tyr Ala Met Ile Gly Asn Asp Val Cys Ser Gly Lys 1163             1172             1181             1190             1199
AGT GAC CCA GTC CCA GCC ATG ACC ACT CCT GAG AAA CTC TAC TCC AAC
Ser Asp Pro Val Pro Ala Met Thr Thr Pro Glu Lys Leu Tyr Ser Asn 1208         1217             1226             1235             1244
GTC ATG CAG ACT CTG AAG CAT CTA AAT TCC CAC CTG CCC AAT GGA TCC
Val Met Gln Thr Leu Lys His Leu Asn Ser His Leu Pro Asn Gly Ser 1254     1262             1271             1280             1289             1298
CAT GTT ATT TTG TAT GGC TTA CCA GAT GGA ACC TTT CTC TGG GAT AAT
His Val Ile Leu Tyr Gly Leu Pro Asp Gly Thr Phe Leu Trp Asp Asn 1307         1316             1325             1334             1343
TTG CAC AAC AGA TAT CAT CCT CTC GGC CAG CTA AAT AAA GAC ATG ACC
Leu His Asn Arg Tyr His Pro Leu Gly Gln Leu Asn Lys Asp Met Thr
```

*FIG. 4B.*

```
     1352           1361           1370           1379           1388
TAT GCG CAG TTG TAC TCC TTC CTG AAC TGC CTC CAG GTC AGC CCC TGC
Tyr Ala Gln Leu Tyr Ser Phe Leu Asn Cys Leu Gln Val Ser Pro Cys 1398       1406           1415           1424           1433           1442
CAC GGC TGG ATG TCT TCC AAC AAG ACG TTG CGG ACT CTC ACT TCA GAG
His Gly Trp Met Ser Ser Asn Lys Thr Leu Arg Thr Leu Thr Ser Glu 1451           1460           1469           1478           1487
AGA GCA GAG CAA CTC TCC AAC ACA CTG AAA AAA ATT GCA GCC AGT GAG
Arg Ala Glu Gln Leu Ser Asn Thr Leu Lys Lys Ile Ala Ala Ser Glu 1496           1505           1514           1523           1532
AAA TTT ACA AAC TTC AAT CTT TTC TAC ATG GAT TTT GCC TTC CAT GAA
Lys Phe Thr Asn Phe Asn Leu Phe Tyr Met Asp Phe Ala Phe His Glu 1542       1550           1589           1568           1577           1586
ATC ATA CAG GAG TGG CAG AAG AGA GGC GGA CAG CCC TGG CAG CTC ATC
Ile Ile Gln Glu Trp Gln Lys Arg Gly Gly Gln Pro Trp Gln Leu Ile 1595           1604           1613           1622           1631
GAG CCC GTG GAT GGA TTC CAC CCC AAC GAG GTG GCT TTG CTG TTG TTG
Glu Pro Val Asp Gly Phe His Pro Asn Glu Val Ala Leu Leu Leu Leu 1640           1649           1658           1667           1676
GCG GAT CAT TTC TGG AAA AAG GTG CAG CTC CAG TGG CCC CAA ATC CTG
Ala Asp His Phe Trp Lys Lys Val Gln Leu Gln Trp Pro Gln Ile Leu 1686       1694           1703           1712           1721           1730
GGA AAG GAG AAT CCG TTC AAC CCC CAG ATT AAA CAG GTG TTT GGA GAC
Gly Lys Glu Asn Pro Phe Asn Pro Gln Ile Lys Gln Val Phe Gly Asp 1739           1748       1757
CAA GGC GGG CAC TGAGAATTCG TCGAC
Gln Gly Gly His
          575
```

*FIG. 4C.*

METHOD FOR PRODUCING ACYLOXYACYL HYDROLASE

TECHNICAL FIELD

The present invention relates to DNA sequences encoding acyloxyacyl hydrolase, DNA constructs capable of directing the expression of acyloxyacyl hydrolase and methods for producing acyloxyacyl hydrolase.

BACKGROUND OF THE INVENTION

Gram-negative septicemia, the clinical consequence of gram-negative bacterial invasion into the blood stream or tissue, occurs at a frequency of between 71,000 and 300,000 cases annually in the United States. Approximately forty percent of septicemia cases are associated with septic shock, a serious and rapidly developing complication of septicemia. Septic shock is characterized by hypotension, oliguria, coagulation defects, respiratory failure, and death.

The complex array of inflammatory responses in animals elicited by gram-negative bacteria is believed to be provoked by lipopolysaccharides (LPS) present in the outer membranes of these bacteria. Typically, an LPS molecule consists of an O polysaccharide, an R-core oligosaccharide, and lipid A. The structure of lipid A is highly conserved across a wide range of bacterial genera and is generally believed to be responsible for most of the biological activities of LPS. LPS is believed to provoke a number of both toxic and beneficial inflammatory responses and is believed to be responsible for the interaction of bacteria with target cells, which include macrophages, neutrophils and endothelial cells. While the toxic responses include hypotension, coagulation disturbances and death, beneficial responses include enhanced antibody synthesis, mobilization of phagocytes and acute phase protein synthesis.

Presently, there are no vaccines to immunize at-risk populations against septicemia. Current treatment of septicemia relies heavily on early diagnosis followed by antibiotic therapy. Septic shock patients are treated symptomatically with concurrent antibiotic therapy because of the rapid onset and severity of the symptoms associated with gram-negative septicemia. Current treatments consist of first administering a best guess antibiotic followed by identification through blood cultures and adjustment of antibiotic treatment; however, such a treatment regime does not inactivate the LPS which continue to induce their toxic effects.

Immunotherapy has been suggested as a treatment for gram-negative septicemia. Ziegler et al. (*New Eng. J. Med.* 307: 1225–1230, 1982) conducted a randomized, controlled trial using human anti-core LPS antiserum which demonstrated that immune serum reduced bacteremic mortality. The use of a human polyclonal antisera has significant drawbacks. In addition, the standardization of such preparations is difficult and there is the risk of transmitting viral infections such as HIV or hepatitis. Preparations of monoclonal antibodies have been used to treat septicemia, but the efficacy of such treatment is not undisputed.

Neutrophils have been shown to contain an enzyme, acyloxyacyl hydrolase (AOAH), that partially deacylates the lipid A portion of *Salmonella typhimurium* LPS by removing secondary fatty acyl chains (Hall and Munford, *Proc. Natl. Acad. Sci. USA* 80: 6671–6675, 1983). AOAH has been shown to contain two disulfide-linked subunits with apparent molecular weights of 50,000 and between 14,000–20,000 (Munford and Hall, *J. Biol. Chem.* 264: 15613–15619, 1989). The large subunit has been shown to be glycosylated. Munford and Hall (*Science* 234: 203–205, 1986) showed that when rabbits were injected intradermally with AOAH-treated LPS, and subsequently challenged with an intravenous injection of untreated LPS there was little or no hemorrhagic necrosis of the skin at the intradermal injection site. In contrast, rabbits that were initially injected with untreated LPS exhibited necrosis. AOAH-treated LPS, while reducing the LPS toxicity 100-fold, was found to reduce stimulation of mitogenesis of $\beta$-lymphocytes by only a factor of 12. Munford and Hall (U.S. Pat. No. 4,929,604) have suggested that AOAH may be useful in treating/preventing septic shock caused by gram-negative bacteria.

The purification of AOAH from neutrophils as reported by Munford and Hall (*J. Biol. Chem.*, ibid.) has a number of disadvantages. Although AOAH has been purified from a cultured human premyelocytic cell line, HL-60, and peripheral blood monocytes and neutrophils, it is only a trace protein, accounting for less than 0.001% of the protein in cell lysate. The purification method is a labor intensive, multi-step protocol that does not lend itself to commercial scale-up. A preparation of 9.5 µg of AOAH, accounting for 7.8% of the original activity, was purified from approximately $5 \times 10^{11}$ cells grown in 150 liters of media over a period of 2 months (Munford and Hall, ibid.). In addition, not all HL-60 cell lines are inducible to produce AOAH and AOAH specific activity fluctuates 2–3 fold as the cells are passaged. Purification of AOAH from peripheral blood neutrophils and monocytes has the risk of co-purifying infective agents such as the hepatitis viruses, HIV-1 and other viral agents, and the availability of large amounts of blood is not always assured.

There is therefore a need in the art for a method of producing relatively large amounts of pure preparations of AOAH, which would be useful as, *inter alia*, a therapeutic agent in the treatment of septic shock and for producing LPS vaccines. The present invention fulfills these and other related needs through the use of recombinant DNA technology, thus eliminating the problem of viral contamination and providing commercially feasible quantities of biologically active recombinant AOAH.

SUMMARY OF THE INVENTION

Briefly stated, the present invention discloses isolated DNA sequences encoding acyloxyacyl hydrolase (AOAH). In one embodiment of the invention, the DNA sequence is a cDNA sequence. Certain embodiments of the invention disclose representative DNA sequences encoding AOAH including the DNA sequence which comprises the sequence from nucleotide 354 to nucleotide 1976 of either FIGS. 1 or 2, the DNA sequence of FIG. 3 from nucleotide 389 to nucleotide 2011 or the DNA sequence of FIG. 4 from nucleotide 120 to nucleotide 1742. Within other embodiments of the invention, representative DNA sequences encoding AOAH encodes the amino acid sequence from Leucine, number 35 to Histidine, number 575 of FIGS. 1, 2, 3 or 4. In another embodiment of the invention, the DNA sequence further codes for the amino acid sequence $(R_1)_n$—$R_2$—$R_3$—$R_4$, wherein $R_1$, $R_2$, $R_3$ and $R_4$ are lysine (lys) or arginine (arg) and n is a integer between 0 and 4.

In yet another embodiment of the invention, DNA sequences encode the small subunit of AOAH. In certain aspects the DNA sequences encoding the small subunit of AOAH may be encoded by the DNA sequence from nucleotide 354 to nucleotide 719 of FIGS. 1 or 2, the DNA sequence of FIG. 3 from nucleotide 389 to nucleotide 754 or the DNA sequence of FIG. 4 from nucleotide 120 to nucleotide 485. Within other embodiments, a DNA sequence encoding the small subunit of AOAH may encode the amino acid sequence from Leucine, number 35 to Arginine, number 154 of FIGS. 1, 2, 3 or 4.

Other embodiments of the invention relate to DNA sequences encoding the large subunit of AOAH. In certain embodiments of the invention, the large subunit of AOAH may be encoded by the DNA sequence from nucleotide 720 to nucleotide 1976 of FIGS. 1 or 2, the DNA sequence of FIG. 3 from nucleotide 755 to nucleotide 2011 or the DNA sequence of FIG. 4 from nucleotide 486 to nucleotide 1742. Other embodiments of the invention disclose a DNA sequence encoding the large subunit of AOAH comprising the amino acid sequence from Serine, number 157 to Histidine, number 575 of FIGS. 1, 2, 3 or 4.

In certain embodiments of the invention, DNA constructs containing information necessary to direct the expression of AOAH are disclosed. In one aspect of the invention, DNA sequences encoding secretory signal peptides are included in the DNA constructs. In certain preferred embodiments, the signal peptides are the amino acid sequences Met-Glu-Ser-Pro-Trp-Lys-Ile-Leu-Thr-Val-Ala-Pro-Leu-Phe-Leu-Leu-Leu-Ser-Pro-Gly-Ala-Trp-Ala-Ser-Pro-Ala-Asn-Asp-Asp-Gln-Ser-Arg-Pro-Ser or Met-Glu-Ser-Pro-Trp-Lys-Ile-Leu-Thr-Val-Ala-Pro-Leu-Phe-Leu-Leu-Leu-Ser-Pro-Gly-Ala-Trp-Ala.

Within one embodiment of the invention, eukaryotic host cells containing DNA constructs containing information necessary for the expression of AOAH are disclosed. In another embodiment of the invention, eukaryotic host cells are transformed or transfected with a first DNA construct containing the information necessary to direct the expression of the large subunit of AOAH and a second DNA construct containing the information necessary to direct the expression of the small subunit of AOAH. Within certain preferred embodiments, the eukaryotic host cells are cultured mammalian cells or yeast cells.

In yet another embodiment of the invention, methods are described for producing the AOAH using the eukaryotic host cells transformed or transfected with DNA constructs containing the information necessary to direct the expression of AOAH or with a first DNA construct containing the information necessary to direct the expression of the large subunit of AOAH and a second DNA construct containing the information necessary to direct the expression of the small subunit of AOAH. Eukaryotic cells so transformed or transfected are then cultured under conditions conducive to expression of the AOAH, which is then isolated from the cells or culture.

BRIEF DESCRIPTION OF THE DRAWINGS

FIGS. 1A–1C illustrates the nucleotide sequence and deduced amino acid sequence of a representative sequence encoding AOAH, the C/26 AOAH cDNA. The small arrow denotes the putative start of the small subunit. The large arrow denotes the putative start of the large subunit.

FIGS. 2A–2C collectively illustrate the nucleotide sequence and deduced amino acid sequence of a representative sequence encoding AOAH, the 4–33 AOAH cDNA. Symbols used are as in FIG. 1.

FIGS. 3A–3D illustrate the consensus AOAH nucleotide sequence and deduced amino acid sequence. Symbols used are as in FIG. 1.

FIGS. 4A–4C collectively illustrate the nucleotide sequence and deduced amino acid sequence of the AOAH1 cDNA. Symbols used are as in FIG. 1.

DETAILED DESCRIPTION OF THE INVENTION

Figure 5:
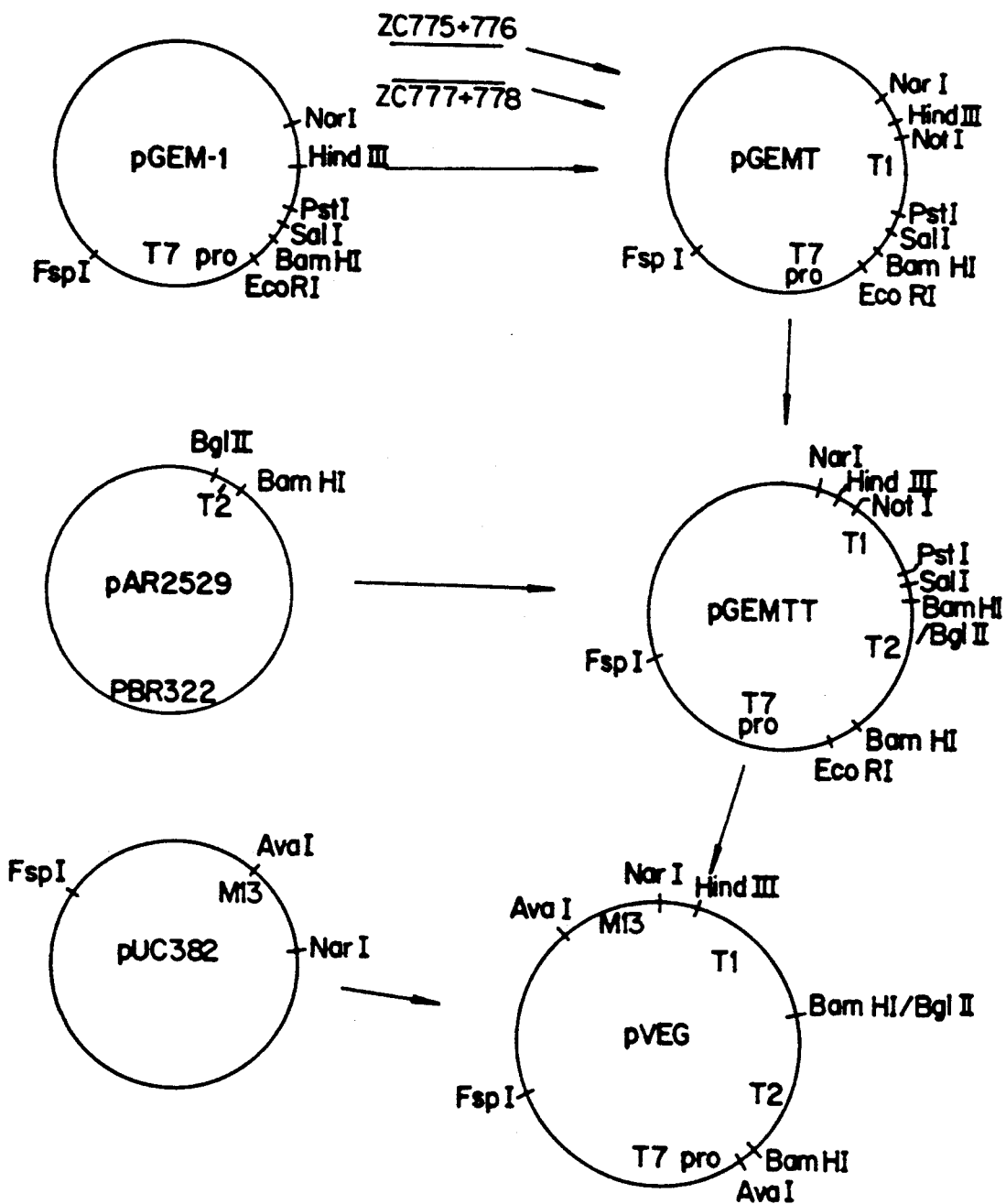
FIG. 5 illustrates the construction of plasmid pVEG. Symbols used are T7 pro, the T7 promoter; T1 and T2, synthetic and native T7 terminators, respectively; M13, M13 intergenic region.

Prior to setting forth the invention, it may be helpful to an understanding thereof to set forth definitions of certain terms to be used hereinafter.

DNA construct: A DNA molecule, or a clone of such a molecule, which has been constructed through human intervention to contain sequences arranged in a way that would not otherwise occur in nature.

Secretory Signal Sequence: A DNA sequence encoding a secretory peptide. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly synthesized proteins. Very often the secretory peptide is cleaved from the mature protein during secretion. Processing sites may be encoded within the secretory peptide or may be added to the secretory peptide by, for example, in vitro mutagenesis or ligation of a linker sequence. Certain secretory peptides may be used in concert to direct the secretion of polypeptides and proteins. One such secretory peptide that may be used in combination with other secretory peptides is the third domain of the yeast Barrier protease. As used herein, the term "secretory peptide" includes at least a functional portion of a naturally occurring secretory peptide.

Secretory peptides may or may not include a pro peptide. In general, pro peptides facilitate post-translational modifications of the proteins or target a protein to a particular organelle. As used herein, the secretory pathway is understood to include the transport pathway of proteins into lysosomes and vacuoles, the transport pathway of proteins into the periplasmic space and the export pathway of proteins into the medium.

Expression Vector: A DNA construct containing elements which direct the transcription and translation of DNA sequence encoding polypeptides of interest. Such elements include promoters, enhancers, transcription terminators and polyadenylation signals. By virtue of the inclusion of these elements within DNA constructs, the resulting expression vectors contain the information necessary to direct the expression and/or secretion of the encoded polypeptides. Expression vectors further contain genetic information that provides for their replication in a host cell, either by autonomous replication or by integration into the host genome. Examples of expression vectors commonly used for recombinant DNA are plasmids and certain viruses, although they may contain elements of both. They also may include one or more selectable markers.

Transfection or transformation: The process of stably and hereditably altering the genotype of a recipient cell or microorganism by the introduction of purified DNA. This is typically detected by a change in the phenotype of the recipient organism. The term "transformation" is generally applied to microorganisms, while "transfection" is generally used to describe this process in cells derived from multicellular organisms.

Cultured cell: A cell capable of being grown in liquid or solid media over a number of generations. In the case of cells derived from multicellular organisms, a cultured cell is a cell isolated from the organism as a single cell, a tissue, or a portion of a tissue.

As noted above, AOAH is a disulfide-linked dimer composed of a large subunit of approximately 50 kD and a small subunit of between 14 and 20 kD. As disclosed as part of the present invention, AOAH is encoded by a single gene. AOAH is a trace protein making current AOAH purification procedures time consuming and expensive. (Munford and Hall, J. Biol. Chem. ibid.; suggest that there are approximately 2,500 molecules per cell.) AOAH removes secondary fatty acyl chains that are linked to the hydroxyl groups of the 3-hydroxytetradecanoyl residues of lipid A.

The present invention discloses representative DNA and amino acid sequences encoding AOAH. Sequences encoding AOAH include those sequences resulting in minor variations in amino acid sequence, such as those due to genetic polymorphism, differences between species, and those in which blocks of amino acids have been added, deleted or replaced without substantially altering the biological activity of the proteins.

In other instances one may employ such changes in the sequence of recombinant AOAH to substantially decrease or even increase the biological activity of AOAH, depending on the intended use of the preparation. The term "biological activity" means the ability to remove secondary fatty acyl groups from LPS. The biological activity of AOAH may be assayed by, for example, measuring the hydrolysis of tritiated-fatty acids from $^3$H-acyl, $^{14}$C-glucosamine-labeled LPS as described by U.S. Pat. No. 4,929,604, which is incorporated herein by reference. Changes in the AOAH coding sequence will result in a polypeptide sufficiently duplicative as to retain the biological activity of native AOAH.

Based on the deduced amino acid sequence of the small AOAH subunit, partial homology was found between the small subunit and sphingolipid activator protein (SAP) precursor. SAPs, which are produced by the proteolytic processing of a SAP precursor into four small subunits, are co-factors required for the activity of lysosomal hydrolases in the degradation of sphingolipids. The SAP precursor and the lysosomal hydrolases with which the SAPs work are encoded by different genes. The AOAH small subunit also shows striking homology to sulfated glycoprotein 1, human pulmonary surfactant protein B and canine pulmonary surfactant protein B. The alignment of the AOAH small subunit sequence with these other proteins shows that four out of the six SAP cysteines have counterparts in the AOAH sequence.

Comparison of the deduced amino acid sequence of the large AOAH subunit has elucidated a partial homology between the large subunit and the consensus essential serine sequence of pancreatic lipases. Pancreatic lipases have been shown to share a significant homology around the essential serine that extends 6 residues on either side of the essential serine (Mickel et al., J. Biol. Chem. 264: 12895–12901, 1989 and Lowe et al., J. Biol. Chem. 264: 20042–20046, 1989).

It is an object of the present invention to provide DNA sequences encoding acyloxyacyl hydrolase (AOAH). An additional object of the present invention is to provide DNA sequences encoding the large subunit of AOAH and the small subunit of AOAH. It is also an object of the present invention to provide methods for producing AOAH from recombinant host cells. A feature of the present invention is a DNA construct capable of directing the expression of AOAH. It is a further feature of the present invention to have eukaryotic host cells containing DNA constructs capable of directing the expression of AOAH. The present invention provides the advantage that AOAH is produced at levels substantially higher than that found in neutrophils. In addition, the present invention provides the advantage of producing AOAH that is exported from a recombinant cell into the medium where it will be more easily isolated. Thus the recombinant AOAH may be produced apart from molecules which which it is typically associated in neutrophils, thereby facilitating the preparation of substantially pure recombination AOAH, as discussed hereinbelow. It is a further advantage of the present invention to produce AOAH from cultured recombinant cells, thus eliminating the risk of transmission of viral infections while providing a method for producing large amounts of biologically active AOAH or AOAH capable of being activated.

Although DNA sequences encoding AOAH may be isolated from cDNA and/or genomic libraries, initial attempts by the inventors to isolate AOAH cDNA sequences using a monoclonal antibody against AOAH or using a mixed family of probes based on the genetic code for the AOAH amino acid sequence were unsuccessful. The high redundancy of the genetic code for the disclosed amino acid sequence and the trace amount of AOAH present in the cell are believed to contribute to the failure of traditional cDNA screening methods.

In one aspect of the present invention, polynucleotide sequences encoding AOAH, and particularly DNA sequences, are isolated from amplified cDNA sequences using polymerase chain reactions (PCRs). Suitable sources from which RNA for the preparation of cDNA may be isolated include, for example, a cultured promyelocytic cell line such as HL-60 (ATCC CRL 240), a cultured lymphoma cell line such as U-937 (ATCC CRL 1593), peripheral blood monocytes or neutrophils, peripheral blood leukocytes of rabbits, chicken, pigs, mice and cows, with U-937 cells being particularly preferred.

A representative method for isolating a DNA sequence encoding AOAH involves the use of PCR amplification. In the absence of known AOAH DNA sequences, synthetic oligonucleotide primers were designed from an amino acid sequence derived from the amino terminal end of the large subunit of AOAH, designated the core sequence. Due to the high redundancy of the genetic code, the core sequence was unsuitable for designing primers for the direct amplification of AOAH-encoding DNA. To overcome this problem, highly degenerate oligonucleotide primers were designed from amino-terminal and carboxy-terminal portions of the core sequence. To facilitate rescue of the amplified DNA sequence, flanking cloning sequences, such as restriction sites, were included in the primers. These degenerate primers were used to amplify AOAH-encoding sequences from random-primed cDNA prepared from U-937 mRNA using the method essentially described by Lee et al. (*Science* 239: 1288–1291, 1988, incorporated herein by reference). The resulting amplified DNA sequence was sublconed into an cloning vector to facilitate sequence analysis of the core sequence. Suitable cloning vectors include pUC-type plasmids (Marsh et al., *Gene* 32: 481–485, 1984; Messing, *Meth. Enzymol.* 101: 21–77, 1983; Yanisch-Perron et al., *Gene* 33: 103, 1985). A preferred cloning vector is a bacteriophage lambda cloning vector. Particularly preferred lambda cloning vectors are λZAP (Stratagene Cloning Systems, La Jolla, Calif.) and λHG-3 (disclosed hereinbelow).

An oligonucleotide probe corresponding to the core sequence was synthesized and used to probe a random-primed cDNA library prepared from mRNA from HL-60 cells; however, only two partial cDNA clones of approximately 800 and 900 bp were isolated out of $7.2 \times 10^6$ phage clones. Sequence analysis showed that the two clones were overlapping, but had different 5' ends, suggesting the differential splicing of messages. Sequence analysis of the clones suggested that both subunits of AOAH are encoded by a single gene; however, the cDNA were incomplete and did not contain the 3' end of the AOAH coding sequence.

Having obtained only partial cDNA from the λGT11 cDNA library, PCR amplification was used to clone a complete DNA sequence encoding human AOAH. Briefly, cDNA encoding 5' and 3' AOAH sequences were independently isolated from U-937 poly(A)+ RNA. Complementary cDNA was prepared for use as a template for the amplification of 3' AOAH DNA sequences using an oligo-d(T) primer containing a cloning sequence, such as a sequence encoding various restriction sites located 5' to the oligo-d(T) tract to facilitate subcloning. It may be preferable to prepare a double-stranded cDNA as a template for amplifying 3' AOAH DNA from the oligo-d(T)-primed cDNA by synthesizing a second strand using a primer encoding a sequence corresponding to a portion of the core sequence.

Double-stranded cDNA for use as a template for the amplification of 5' AOAH DNA sequences was prepared from U-937 poly(A)+ RNA using an antisense primer encoding a sequence corresponding to a portion of the core sequence. The resulting cDNA was G-tailed using the method essentially described by Maniatis et al. (*Molecular Cloning: A Laboratory Manual,* Cold Spring Harbor, 1982). The second strand of the G-tailed cDNA was synthesized using a poly-d(C) primer containing a cloning sequence such as a sequence encoding various restriction sites 5' to the poly-d(C) track to facilitate subcloning.

Due to the rarity of the AOAH message, the 5' and 3' templates were enriched for cDNA encoding the 5' and 3' AOAH coding sequences. The cDNA preparations were first fractionated on a 1% low melt alkaline agarose gel. The lane containing the 3' cDNA was cut into 12 0.5-cm fragments, and the lane containing the 5' cDNA was cut into 8 1-cm fragments. The cDNA was eluted and amplified. The 3' AOAH cDNA was amplified using a sense primer encoding a portion of the core sequence and a primer encoding a portion of the oligo-d(T) primer. The 5' AOAH cDNA was amplified using a primer encoding the antisense core sequence and a primer encoding a portion of the oligo-d(C) primer. In cases where the oligo-d(T) and oligo-d(C) primers contain cloning sequences, preferred primers will encode the cloning sequences. Southern blot analysis using the method essentially described by Maniatis et al. (ibid.) was carried out on a portion of each PCR reaction using the antisense primer as a probe. Evidence from the Southern analysis narrowed the suitable cDNA to gel fragment #3 for the amplification of 3' AOAH coding sequences and fragment #4 for the amplification of 5' AOAH coding sequences.

Primers for the amplification of DNA sequences encoding 5' and 3' AOAH coding sequences were designed essentially as described by Hagen (copending U.S. patent application Ser. No. 07/320,191, which is incorporated herein by reference). Briefly, primers containing sequences termed "prime sequences" were used to facilitate the subcloning of the amplified DNA sequences, in a directional manner, into cloning vectors. Oligonucleotide primers were designed using the formula $X_n T_y N_m$, wherein $X_n$ is a sequence of deoxynucleotide monophosphates other than deoxythymidine monophosphate (d(T)) from 3 to about 25 nucleotides in length, preferably about 12 to about 15 nucleotides in length, and $T_y$ is one or more, preferably 2 or more, deoxythymidine monophosphates. $N_m$ is an oligodeoxynucleotide that is the same or complementary to a terminal cDNA sequence. A 3' prime sequence, $X_1 T_y$, was designed for use as the 3' sequence of a 3' prime primer, and a 5' prime sequence, $X_2 T_y$, was designed for use as the 5' sequence of a 5' prime primer wherein $X_1$ and $X_2$ are as defined above, and the sequences of $X_1$ and $X_2$ are different and sufficiently noncomplementary to prevent them from annealing to each other as necessary for efficient cloning. In addition, $X_1$ and $X_2$ are non-palindromic.

Two prime primers, $X_1 T_y N_1$ and $X_2 T_y N_2$, were designed for the amplification of 3' AOAH sequences, and two prime primers, $X_1 T_y N_3$ and $X_2 T_y N_4$, were designed for the amplification of 5' AOAH sequences, wherein $X_1$, $X_2$ and $T_y$ are as defined above; $N_1$ is an oligodeoxynucleotide encoding a portion of the oligo-d(T) primer; $N_2$ is an oligodeoxynucleotide corresponding the sense strand of the core sequence; $N_3$ is an oligodeoxynucleotide corresponding to the antisense strand of the core sequence; and $N_4$ is an oligodeoxynucleotide encoding a portion of the oligo-d(C) primer. The enriched 5' and 3' template cDNA were amplified using the prime primers essentially as described by Frohman et al. (*Proc. Natl. Acad. Sci. USA* 85: 8998–9002, 1988).

Adhesive ends were created on the amplified cDNA by treatment with T4 DNA polymerase in the presence of dATP. The treated cDNA was gel purified and subcloned into a vector containing adhesive ends complementary to the prime sequences encoded by the amplified cDNA. The DNA inserts were analyzed by restriction analysis and DNA sequence analysis. The sequence analysis confirmed that the amplified DNAs overlapped the core sequence and established a full length sequence of 2290 bp.

A full length cDNA was amplified using 5' prime primers and 3' prime primers according to the formulas $X_1T_yN_5$ and $X_2T_yN_6$ wherein $X_1$, $X_2$ and Ty are as defined above; $N_5$ is a oligonucleotide sequence corresponding to the sense strand of the 5' untranslated sequence of AOAH; and $N_6$ is an antisense oligonucleotide sequence corresponding to the 3' untranslated sequence of AOAH. The primers were used to amplify the cDNA from fragment #3. The resulting PCR product was subcloned into an cloning vector as described above. The PCR inserts were analyzed by restriction analysis and DNA sequence analysis. Comparison of the full length AOAH cDNA and the partial AOAH cDNAs generated through PCR amplification and cDNA library screening showed that the PCR reactions incorporated mutations into the full length cDNA. These mutations were corrected by PCR amplification of fragments of template DNA having the correct sequence.

FIGS. 1, 2, and 3 disclose representative nucleotide sequences encoding AOAH. The cDNA's span 2277 bp and encode 575 residues including a 34 residue putative pre-pro region and seven cysteines. Analysis of the deduced amino acid sequence shows a putative cleavage site between the large and small subunits at residue 156.

With the nucleotide and deduced amino acid sequence of human AOAH provided herein, genomic or cDNA sequences encoding AOAH may be obtained from libraries prepared from other mammalian species according to well known procedures. For instance, using oligonucleotide probes from human AOAH, generally of at least about fourteen nucleotides and up to twenty-five or more nucleotides in length; DNA sequences encoding AOAH of other higher eukaryotic species, such as lagomorph, avian, bovine, porcine, murine, etc. may be obtained. If partial clones are obtained, it is necessary to join them in proper reading frame to produce a full length clone, using such techniques as endonuclease cleavage, ligation and loopout mutagenesis.

A DNA sequence encoding AOAH was inserted into a suitable expression vector, which was in turn used to transfect eukaryotic cells. Expression vectors for use in carrying out the present invention will comprise a promoter capable of directing the transcription of a cloned DNA and a transcriptional terminator. The DNA sequences encoding the large and small subunits may also be expressed independently either on the same or different plasmids.

To direct proteins of the present invention into the secretory pathway of the host cell, at least one secretory signal sequence is operably linked to the DNA sequence of interest. Preferred secretory signals include the AOAH secretory signal (pre-pro sequence), the alpha factor signal sequence (pre-pro sequence; Kurjan and Herskowitz, *Cell* 30: 933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3: 439–447, 1983), the α-1-antitrypsin signal sequence (Kurachi et al., *Proc. Natl. Acad. Sci. USA* 78: 6826–6830, 1981), the α-2 plasmin inhibitor signal sequence (Tone et al., *J. Biochem.* (*Tokyo*) 102: 1033–1042, 1987) and the tissue plasminogen activator signal sequence (Pennica et al., *Nature* 301: 214–221, 1983). Alternatively, a secretory signal sequence may be synthesized according to the rules established, for example, by von Heinje (*Eur. J. Biochem* 133: 17–21, 1983; *J. Mol. Biol.* 184: 99–105, 1985; *Nuc. Acids Res* 14: 4683–4690, 1986).

Secretory signal sequences may be used singly or may be combined. For example, a first secretory signal sequence may be used singly or in combination with a sequence encoding the third domain of Barrier (described in co-pending commonly assigned U.S. patent application Ser. No. 104,316, which is incorporated by reference herein in its entirety). The third domain of Barrier may be positioned in proper reading frame 3' of the DNA sequence of interest or 5' to the DNA sequence and in proper reading frame with both the secretory signal sequence and the DNA sequence of interest.

Host cells for use in practicing the present invention include mammalian, avian, plant, insect and fungal cells. Fungal cells, including species of yeast (e.g., Saccharomyces spp., Schizosaccharomyces spp.) or filamentous fungi (e.g., Aspergillus spp., Neurospora spp.) may be used as host cells within the present invention. Strains of the yeast *Saccharomyces cerevisiae* are particularly preferred.

Suitable yeast vectors for use in the present invention include YRp7 (Struhl et al., *Proc. Natl. Acad. Sci. USA* 76: 1035–1039, 1978), YEp13 (Broach et al., *Gene* 8: 121–133, 1979), POT vectors (Kawasaki et al, U.S. Pat. No. 4,931,373, which is incorporated by reference herein), pJDB249 and pJDB219 (Beggs, *Nature* 275: 104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), YRA3 (Botstein et al., *Gene:* 8: 17, 1979), HIS3 (Struhl et al., ibid.) or POT1 (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311) or alcohol dehydrogenase genes (Young et al., in *Genetic Engineering of Microorganisms for Chemicals,* Hollaender et al., (eds.), p. 355, Plenum, New York, 1982 Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^C$ promoter (Russell et al., *Nature* 304: 652–654, 1983; Irani and Kilgore, U.S. patent application Ser. No. 183,130, which is incorporated herein by reference). The expression units may also include a transcriptional terminator. A preferred transcriptional terminator is the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4: 2093–2099, 1985) and the tpiA promoter. An example of a suitable terminator is the ADH3 terminator (McKnight et al., ibid.). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75: 1929–1933, 1978), Yelton et al. (*Proc. Natl. Acad. Sci. USA* 81: 1740–1747, 1984), and Russell (*Nature* 301: 167–169, 1983). The genotype of the host cell will generally contain a genetic defect that is complemented by the selectable marker present on the expression vector. Choice of a particular host and selectable marker is well within the level of ordinary skill in the art.

In a preferred embodiment, a yeast host cell that contains a genetic deficiency in at least one gene required for asparagine-linked glycosylation of glycoproteins is used. Preferably, the yeast host cell contains a genetic deficiency in the MNN9 gene (described in pending, commonly assigned U.S. patent application Ser. Nos. 116,095 and 189,547, which are incorporated by reference herein in their entirety). Most preferably, the yeast host cell contains a disruption of the MNN9 gene. Yeast host cells having such defects may be prepared using standard techniques of mutation and selection. Ballou et al. (*J. Biol. Chem.* 255: 5986–5991, 1980) have described the isolation of mannoprotein biosynthesis mutants that are defective in genes which affect asparagine-linked glycosylation. Briefly, mutagenized yeast cells were screened using fluoresceinated antibodies directed against the outer mannose chains present on wild-type yeast. Mutant cells that did not bind antibody were further characterized and were found to be defective in the addition of asparagine-linked oligosaccharide moieties. To optimize production of the heterologous proteins, it is preferred that the host strain carries a mutation, such as the yeast pep4 mutation (Jones, *Genetics* 85: 23–33, 1977), which results in reduced proteolytic activity.

In addition to fungal cells, cultured mammalian cells may be used as host cells within the present invention. Preferred cultured mammalian cells for use in the present invention include the COS-1 (ATCC CRL 1650), BHK, and 293 (ATCC CRL 1573; Graham et al., *J. Gen. Virol.* 36: 59–72, 1977) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CCL 29.1), NCTC 1469 (ATCC CCL 9.1) and DUKX cells (Urlaub and Chasin, *Proc. Natl. Acad. Sci USA* 77: 4216–4220, 1980).

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41: 521–530, 1985) and the SV40 promoter (Subramani et al., *Mol. Cell. Biol.* 1: 854–864, 1981). Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81: 7041–7045, 1983; Grant et al., *Nuc. Acids Res.* 15: 5496, 1987) and a mouse $V_H$ promoter (Loh et al., *Cell* 33: 85–93, 1983). A particularly preferred promoter is the major late promoter from Adenovirus 2 (Kaufman and Sharp, *Mol. Cell. Biol.* 2: 1304–13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9: 3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse μ enhancer (Gillies, *Cell* 717–728, 1983). Expression vectors may also include sequences encoding the adenovirus VA RNAs.

The processing of the AOAH into the mature two chain form may be enhanced by modifying the cleavage site between the large and small subunits of AOAH to enhance cleavage of the precursor to the two-chain form. Modified cleavage sites for AOAH include amino acid sequences of the formula $(R_1)_n-R_2-R_3$, wherein $R_1$ through $R_3$ are lysine (Lys) or arginine (Arg) and n is an integer from 0 to 4, located between the large and small subunits of AOAH. Processing of AOAH by cleavage after a dibasic dipeptide such as Arg-Lys and subsequent removal of these amino acids may be enhanced by introducing the *S. cerevisiae* KEX1 and/or KEX2 genes into the host cell as described in pending, commonly assigned U.S. patent applications Ser. Nos. 07/317,205; 130,370; and 144,357, and published EP 319,944 which are incorporated herein by reference. The KEX2 gene encodes an endopeptidase that cleaves after a dibasic amino acid sequence (Fuller et al., in Leive, ed., *Microbiology:* 1986, 273–278, 1986); the expression of the KEX1 gene (Dmochowska et al., *Cell* 50: 573–584, 1987) results in the subsequent removal of these dibasic amino acids. A DNA sequence encoding KEX2 has been deposited with the ATCC, 12301 Parklawn Dr., Rockville, Md. 20852 under accession number 67569. A cultured eukaryotic cell line transfected with one or both of these genes is thus useful for expressing AOAH having a modified cleavage site between the large and small subunits. Processing sites may be inserted between the sequences encoding the large and small subunits by, for example, in vitro mutagenesis.

Cloned DNA sequences may be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973.) Other techniques for introducing cloned DNA sequences into mammalian cells, such as electroporation (Neumann et al., *EMBO J.* 1: 841-845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods for introducing expression vectors encoding AOAH into plant, avian and insect cells are well known in the art. The use of baculoviruses, for example, as vectors for expressing heterologous DNA sequences in insect cells has been reviewed by Atkinson et al. (Pestic. Sci. 28: 215-224,1990). The use of *Agrobacterium rhizogenes* as vectors for expressing genes in plant cells has been reviewed by Sinkar et al. (*J. Biosci.(Banglaore)*11: 47-58, 1987).

Host cells containing DNA constructs of the present invention are then cultured to produce AOAH. The cells are cultured according to standard methods in a culture medium containing nutrients required for growth of mammalian or yeast host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M., preferably at 0.5M or 1.0M. Cultured mammalian cells are generally cultured in commercially available serum-containing or serum-free media. Selection of a medium appropriate for the particular cell line used is within the level of ordinary skill in the art.

The AOAH produced according to the present invention may be purified by affinity chromatography on an antibody column using antibodies directed against AOAH. Additional purification may be achieved by conventional chemical purification means, such as liquid chromatography, gradient centrifugation, and gel electrophoresis, among others. Methods of protein purification are known in the art (see generally, Scopes, R., *Protein Purification*, Springer-Verlag, N.Y. (1982), which is incorporated herein by reference) and may be applied to the purification of the recombinant AOAH described herein; see also a purification protocol described in U.S. Pat. No. 4,929,604. Substantially pure recombinant AOAH of at least about 50% is preferred, at least about 70-80% more preferred, and 95-99% or more homogeneity most preferred, particularly for pharmaceutical uses. Once purified, partially or to homogeneity, as desired, the recombinant AOAH may then be used therapeutically.

The recombinant AOAH molecules of the present invention and pharmaceutical compositions thereof are useful for administration to mammals, including humans, to treat a variety of conditions associated with the toxicity of gram-negative bacterial infections. For instance, although a gram-negative bacterial infection can itself be treated with conventional antibiotics, the AOAH preparations described herein may be used to treat or prevent the LP toxicity associated with such infections such as disseminated intravascular coagulation and others as described above.

The pharmaceutical compositions are intended for parenteral, topical, oral or local administration for prophylactic and/or therapeutic treatment. Preferably, the pharmaceutical compositions are administered parenterally, i.e., intravenously, subcutaneously, or intramuscularly. Thus, this invention provides compositions for parenteral administration which comprise a solution of the recombinant AOAH molecules dissolved in an acceptable carrier, preferably an aqueous carrier. A variety of aqueous carriers may be used, e.g., water, buffered water, 0.4% saline, 0.3% glycine, 20-30% glycerol and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The concentration of recombinant AOAH in these formulations can vary widely, i.e., from less than about 0.5%, usually at or at least about 1% to as much as 15 or 20% by weight and will be selected primarily by fluid volumes, viscosities, etc., in accordance with the particular mode of administration selected. Actual methods for preparing parenterally administrable compounds will be known or apparent to those skilled in the art and are described in more detail in for example, Remington's Pharmaceutical Science, 16th ed., Mack Publishing Company, Easton, Pa. (1982), which is incorporated herein by reference.

The compositions containing the recombinant AOAH molecules can be administered for prophylactic and/or therapeutic treatments. In therapeutic applications, compositions are administered to a patient already suffering from a gram-negative bacterial disease in an amount sufficient to cure or at least partially arrest the effects of LPS toxicity associated with the disease and its complications. An amount adequate to accomplish this is defined as "therapeutically effective dose." Amounts effective for this use will depend on the severity of the gram-negative infection and the general state of the patient but generally range from about 1 µg to about 10 mg of recombinant AOAH per 70 kg of body weight. It must be kept in mind that the materials of the present invention may generally be employed in serious bacterial disease states, that is, life-threatening or potentially life threatening situations. In such cases, in view of the minimization of extraneous substances and the specificity of the recombinant AOAH made feasible by this invention, it is possible and may be felt desireable by the treating physician to administer substantial excesses of these recombinant AOAH compositions.

In prophylactic applications, compositions containing the recombinant AOAH are administered to a patient susceptible to or otherwise at risk of a gram-negative disease to enhance the patient's own anti-bacterial-/anti-LPS capabilities. Such an amount is defined to be a "prophylactically effective dose." In this use, the precise amounts will again depend on the patient's state of health.

Single or multiple administrations of the compositions can be carried out with the dose levels and pattern being selected by the treating physician. In any event, the pharmaceutical formulations should provide a quantity of recombinant AOAH of this invention sufficient to effectively treat the patient.

To summarize the examples which follow, Example 1 describes the construction of cloning and expression vectors. Example 2 describes cloning of DNA sequences encoding human AOAH. Example 3 describes the expression of AOAH in mammalian cells.

The following examples are offered by way of illustration and not by way of limitation.

EXAMPLES

Restriction endonucleases and other DNA modification enzymes (e.g., T4 polynucleotide kinase, calf alkaline phosphatase, DNA polymerase I (Klenow fragment), T4 polynucleotide ligase) were obtained from Boehringer Mannheim Biochemicals, Bethesda Research Laboratories (BRL) and New England Biolabs and were used as directed by the manufacturer, unless otherwise noted.

Oligonucleotides were synthesized on an Applied Biosystems Model 380A DNA synthesizer and purified by polyacrylamide gel electrophoresis on denaturing gels. *E. coli* cells were transformed as described by Maniatis et al. (*Molecular Cloning: A Laboratoty Manual*, Cold Spring Harbor Laboratory, 1982, incorporated by reference herein). M13 and pUC cloning vectors and host strains were obtained from BRL.

EXAMPLE 1

Construction of Cloning and Expression Vectors

A. Construction of pVEG

To permit transcription of cloned cDNA without prior endonuclease digestion, bacteriophage T7 transcriptional terminators were added to a cloning vector. The sequence of the putative T7 RNA transcription terminator, which lies between gene 10 and gene 11 of bacteriophage T7, is disclosed by Dunn and Studier (*J. Mol. Biol.* 166: 477–536, 1983). As shown in FIG. 5, four synthetic oligonucleotides were designed from this sequence and ligated into the vector pGEM-1 (obtained from Promega Biotec, Madison, Wis.), a plasmid containing a bacterial origin of replication, ampicillin resistance gene, and the T7 promoter adjacent to a multiple cloning site. Terminal phosphates were added to the 5' ends of oligonucleotides ZC776 and ZC777 with T4 polynucleotide kinase and ATP, under standard conditions (Maniatis et al. ibid). (The sequences of these and other oligonucleotides referred to herein are shown in Table 1.) After the incubation, the kinase was heat killed at 65° C. for 10 min. Twenty-five nanograms of oligonucleotide ZC775 and 25 ng of oligonucleotide ZC776 were annealed by incubation at 65° C. for 15 minutes, then allowed to cool to room temperature in 500 ml of water. Oligonucleotides ZC777 and ZC778 were similarly annealed. The annealed oligonucleotides were stored at −20° C. until use. The vector pGEM-1 was digested with Pst I and Hind III, and the linearized vector DNA was purified by agarose gel electrophoresis. The synthetic T7 terminator (annealed oligonucleotides ZC775, ZC776, ZC777 and ZC778) was then cloned into pGEM-1. Twenty-five nanograms of vector plus an equal molar amount of each of the annealed oligonucleotides ZC775/ZC776 and ZC777/ZC778 were combined in a 10 µl reaction mix. After an overnight ligation at 14° C., the DNA was transformed into competent *E. coli* JM83 cells, and the transformed cells were selected for ampicillin resistance. Plasmid DNA was prepared from selected transformants by the alkaline lysis procedure (Birnboim and Doly, *Nuc.Acids Res.* 7: 1513–1523, 1979). A portion of the DNA from these samples was cut with Pst I and Hind III and analyzed on a 4% polyacrylamide gel to identify clones that released an 80 bp Pst I-Hind III fragment. Other diagnostic cuts, such as Eco RI and Not I, were also made. One of the isolates, designated pGEMT, was shown by restriction analysis to contain the T7 terminator fragment.

TABLE 1

| Oligonucleotide | Sequence (5'-3') | | | | | | |
|---|---|---|---|---|---|---|---|
| ZC525 | GGA | ATT | CT | | | | |
| ZC526 | GAT | CAG | AAT | TCC | | | |
| ZC553 | AAT | TGA | TAG | CGG | CCG | CTT | ACT | GCA |
| ZC554 | GTA | AGC | GGC | CGC | TAT | C | | |

TABLE 1-continued

| Oligonucleotide | Sequence (5'-3') | | | | | | | | |
|---|---|---|---|---|---|---|---|---|---|
| ZC775 | GCT | AGC | ATA | ACC | CCT | TGG | GGC | CTC | TAA | ACG |
| | GGT | CT | | | | | | | | |
| ZC776 | CTC | AAG | ACC | CGT | TTA | GAG | GCC | CCA | AGG | GGT |
| | TAT | GCT | AGC | TGC | A | | | | | |
| ZC777 | TGA | GGG | GTT | TTT | TGC | TGA | AAG | GAG | GAA | CTA |
| | TGC | GGC | CGC | A | | | | | | |
| ZC778 | AGC | TTG | CGG | CCG | CAT | AGT | TCC | TCC | TTT | CAG |
| | CAA | AAA | ACC | C | | | | | | |
| ZC1750 | AGG | GAG | ACC | GGA | ATT | CCC | CCC | CCC | C | |
| ZC1751 | AAT | TCT | GTG | CTC | TGT | CAA | G | | | |
| ZC1752 | GAT | CCT | TGA | CAG | AGC | ACA | G | | | |
| ZC2063 | GAT | CCA | AAC | TAG | TAA | AAG | AGC | T | | |
| ZC2064 | CTT | TTA | CTA | GTT | TG | | | | | |
| ZC2465 | ACA | GAC | TGT | TCC | ATA | GCT | AAT | TTA | ATT | TTC |
| | TGG | CAG | AT | | | | | | | |
| ZC2487 | GAC | TCG | AGT | CGA | CAT | CGA | TCA | GTT | TTT | TTT |
| | TTT | TTT | TTT | | | | | | | |
| ZC2488 | GAC | TCG | AGT | CGA | CAT | CGA | TCA | GCC | CCC | CCC |
| | CC | | | | | | | | | |
| ZC2489 | GAC | TCG | AGT | CGA | CAT | CGA | TCA | G | | |
| ZC2631 | AGG | GAG | ACC | GGA | ATT | CCC | ATG | GAA | CAG | TCT |
| | GTG | CCA | TTC | AAA | GAT | GT | | | | |
| ZC2632 | GAC | AGA | GCA | CAG | AAT | TCG | ACT | CGA | GTC | GAC |
| | ATC | GAT | CAG | | | | | | | |
| ZC2633 | AGG | GAG | ACC | GGA | ATT | CGA | CTC | GAG | TCG | ACA |
| | TCG | ATC | AG | | | | | | | |
| ZC2703 | GAC | AGA | GCA | CAG | AAT | TCG | AGC | ACA | CAG | CAT |
| | TGC | ACA | GTC | GT | | | | | | |
| ZC2704 | AGG | GAG | ACC | GGA | ATT | CTC | CAG | CTC | TTT | GTG |
| | TGT | GGC | TCT | C | | | | | | |
| ZC3074 | ACT | TGG | GAA | TTC | GTC | GAC | CAC | CAT | GCA | GTC |
| | CCC | CTG | GAA | A | | | | | | |
| ZC3075 | TTT | ACA | AAA | CTC | GAG | AGT | GTG | | | |
| ZC3076 | CAC | ACT | CTC | GAG | TTT | TGT | AAA | CAG | AAC | ACT |
| | GG | | | | | | | | | |
| ZC3077 | AAC | ATG | GGA | TCC | ATT | GGG | CAG | GTG | GGA | ATT |
| | TAG | ATG | CTT | CAG | AGT | CTG | CAT | GAC | | |
| ZC3078 | CCC | AAT | GGA | TCC | CAT | GTT | ATT | TTG | TAT | GGC |
| | TTA | CCA | GAT | | | | | | | |
| ZC3079 | GGT | GCA | TGG | TCG | ACG | AAT | TCT | CAG | TGC | CCG |
| | CCT | | | | | | | | | |
| ZC3202 | TTA | ATT | TTC | TGG | CAG | ATC | TTG | GCC | | |
| ZC3203 | TAG | GGT | GTG | TAC | TAG | TGG | TGT | CTG | | |

The native T7 terminator form plasmid pAr2529 (Rosenberg et al., Gene 56: 125-135, 1987) was added to plasmid pGEMT. Plasmid pGEMT was digested with Bam HI and plasmid pAR2529 was digested with Bam HI and Bgl II (FIG. 5). The Bam HI-Bgl II terminator fragment from pAR2529 was purified by agarose gel electrophoresis. The terminator fragment was ligated to Bam HI digested pGEMT, and the DNA was transformed into competent E. coli LM1035 cells. Colonies that were ampicillin resistant were inoculated into 5 ml cultures for overnight growth. Plasmid DNA prepared by the alkaline lysis procedure was screened for proper terminator orientation by Bam HI-Sal I digestion and electrophoresis on an 8% polyacrylamide gel. A clone that contained the terminator in the correct orientation, as evidenced by the presence of a 130 bp Bam HI-Sal I fragment, was chosen and named pGEMTT (FIG. 5).

To allow pGEMTT to be packaged as single-stranded DNA in the presence of M13 phage proteins, the M13 intergenic region from pUC382 (similar to pUCl18 and 119 as disclosed by Vieira and Messing, Methods Enzymol. 153: 3-11, 1987) was added to pGEMTT (FIG. 5). Plasmid pGEMTT was digested with Fsp I and Nar I, and the fragment containing the T7 promoter and transcription terminator was purified. Plasmid pUC382 was digested with Fsp I and Nar I, and the fragment encoding the ampicillin resistance gene and the M13 intergenic region was gel purified. These fragments were then ligated together in the presence of T4 DNA ligase. The ligated DNA was transformed into competent E. coli LM1035 cells. Plasmid DNA from twelve ampicillin-resistant colonies was prepared by the alkaline lysis method, and the DNA was screened by digestion with Ava I. The appropriate construction gave two bands, one of 2430 bp and another of 709 bp. One such isolate was chosen and named pVEG.

B. Construction of pVEGT'

Figure 6:
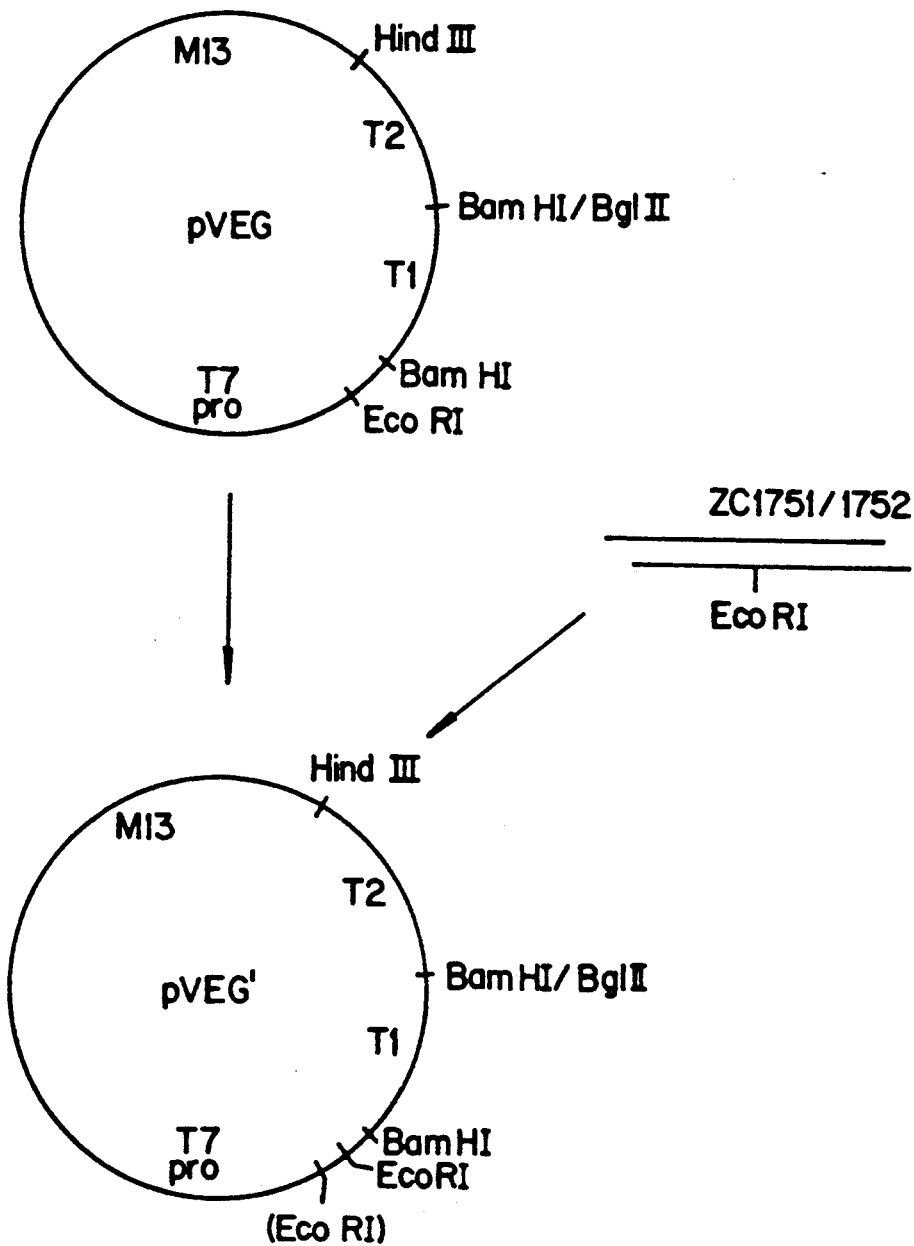
FIG. 6 illustrates the construction of plasmid pVEG'. Symbols used are as in FIG. 5 and parentheses indicate a restriction site destroyed in vector construction.

Synthetic oligonucleotides encoding the prime sequence were added to pVEG between the Bam HI and Eco RI sites (FIG. 6). Plasmid pVEG was digested with Bam HI and Eco RI and the vector fragment was gel purified. Ninety-six nanograms each of oligonucleotides ZC1751 and ZC1752 were annealed in 4.5 µl of 10 mM Tris pH 7.5, 20 mM $MgCl_2$ and 10 mM NaCl at 65° C. for 20 minutes, then the mixture was cooled to room temperature over a period of 30 minutes. The annealed oligonucleotides were ligated to the pVEG vector fragment with T4 DNA ligase and then transformed into competent E. coli LM1035 cells. After growing overnight to develop the colonies, a filter lift was taken of the colonies on the agar plate. The filter was probed with $^{32}$P-labeled oligonucleotide ZC1751. All of the colonies were positive. Plasmid DNA was prepared from cultures grown from 12 of the colonies. The plasmid DNA was screened by digestion with Sst I to verify the absence of the Sst I site between the Eco RI and Bam HI sites of pVEG. All 12 of the plasmid DNAs were negative for Sst I digestion. One of these 12 isolates was chosen and named pVEG'.

Figure 7:
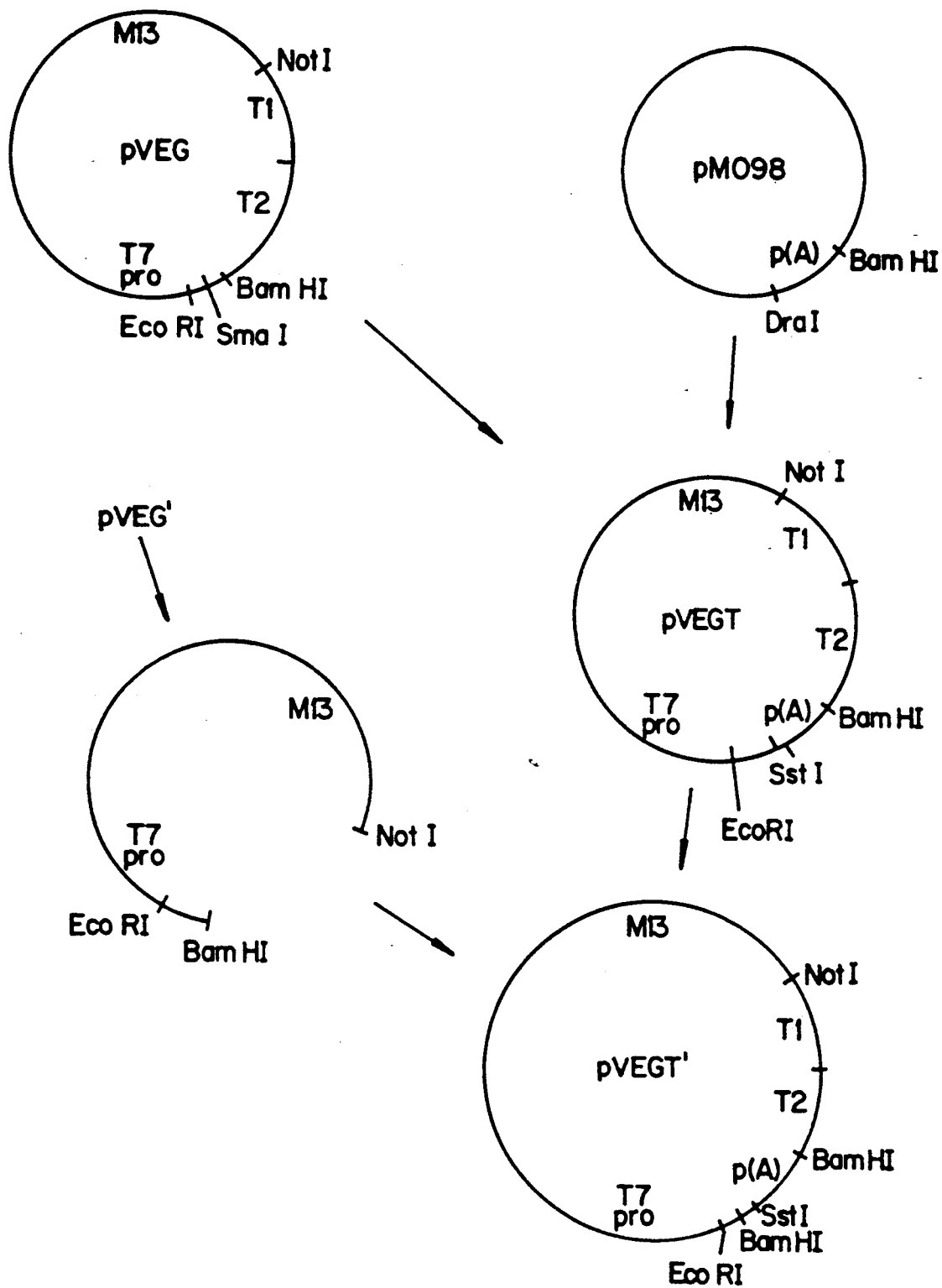
FIG. 7 illustrates the construction of plasmid pVEGT'. Symbols used are as in FIG. 1 and pA, the *Aspergillus niger* polyadenylation sequence.

A polyadenylation sequence derived from an Aspergillus alcohol dehydrogenase cDNA was added to pVEG. As shown in FIG. 7, plasmid pM098 (disclosed in published European patent application EP 272,277 and deposited with American Type Culture Collection under accession number 53428) was digested with Dra I and Bam HI, and the approximately 150 bp poly(A) fragment was purified by agarose gel electrophoresis. This fragment contained mostly poly(A) sequence with very little flanking cDNA. To clone the poly(A) cDNA fragment into pVEG, pVEG was digested with Bam HI and Sma I, and the 3.4 kb vector fragment was gel purified. The vector and poly(A) fragments were ligated together with T4 DNA ligase to produce vector pVEGT (FIG. 7).

Synthetic oligonucleotides encoding the prime sequence were added to pVEGT. To accomplish this, pVEGT was digested with Not I and Sst I, and the 370 bp fragment containing the poly(A) sequence and the two T7 transcriptional terminators was purified by agarose gel electrophoresis. Plasmid pVEG' was digested with Not I and Bam HI, and the 3.2 kb vector fragment was gel-purified. Two oligonucleotides (ZC2063 and ZC2064) that formed, when annealed, a Bam HI-Sst I adapter were synthesized. The two oligonucleotides were individually kinased and annealed, and ligated with the linearized vector and the poly(A)-terminator fragment. The resultant vector, designated pVEGT' (FIG. 3), contained a T7 RNA transcription promoter, an Eco RI cloning site flanked by the prime sequence, a poly(A) tract, and two T7 RNA polymerase terminators.

C. Construction of DVEG

The mammalian expression vector pVAPDBam8 (FIG. 8), an adenovirus-based vector, was the starting material for the construction of a mammalian cell vector containing the directional cloning features. The important elements of this vector are an adenovirus origin of replication, an SV40 enhancer, the adenovirus 2 major late promoter and tripartite leader sequence, a pair of RNA splice sites, a cloning site, and a poly(A) addition sequence. As will be appreciated by those familiar with the art, these elements may be obtained from a variety of sources, and the particular starting materials and manipulations described herein were chosen for convenience. To facilitate the subcloning of Eco RI cloned cDNA into this expression vector, an Eco RI cloning site was added to pVAPDBam8.

Figure 8:
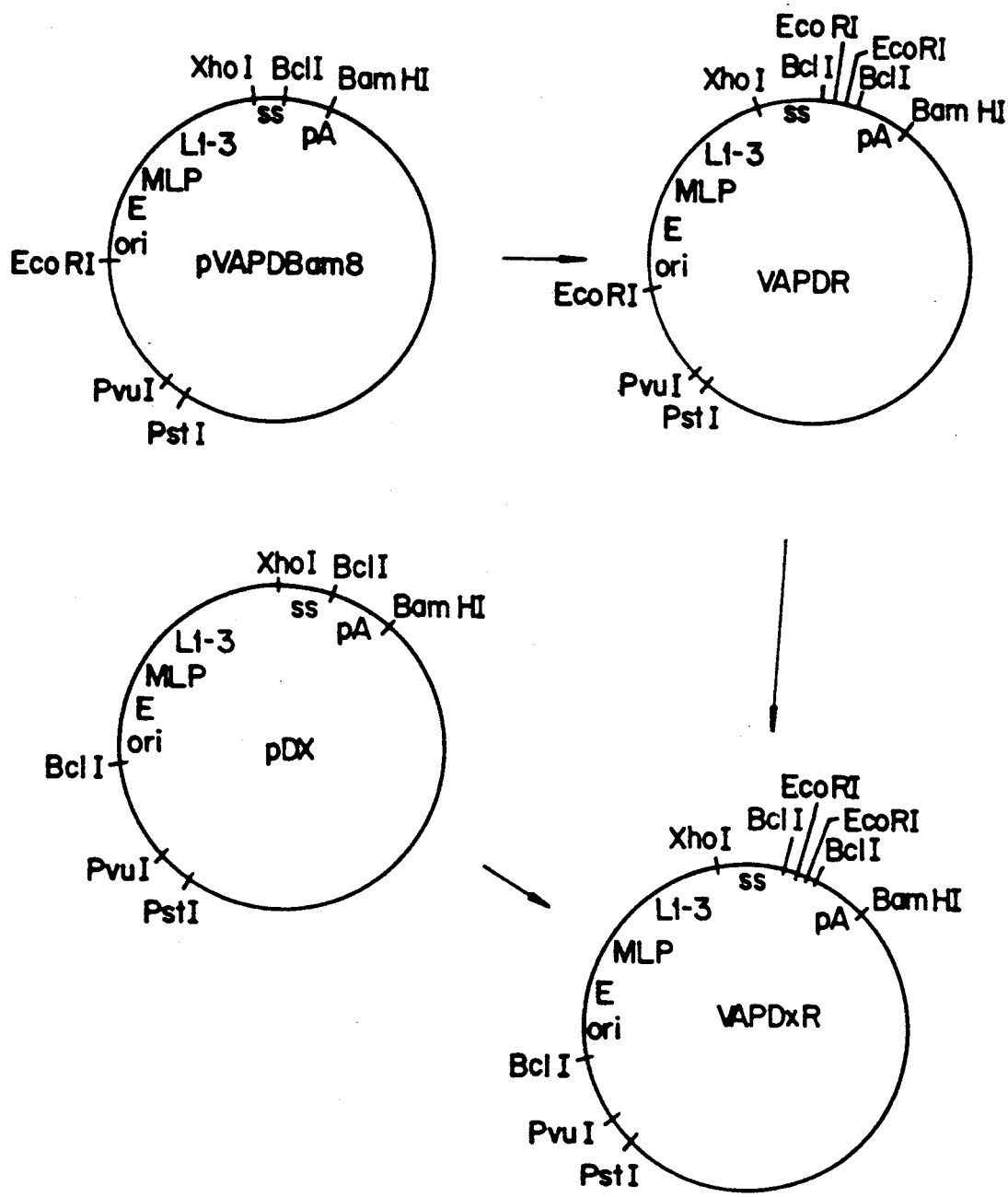
FIGS. 8 and 9 illustrate the construction of plasmids VAPDxR and pDVEG', respectively. Symbols used are ori, the adenovirus 5 0–1 map unit sequence; E, the SV40 enhancer; MLP, the adenovirus 2 major late promoter; L1-3, the adenovirus 2 tripartite leader; SS, a set of RNA splice sites, and pA, the SV40 polyadenylation sequence.

The vector was first modified so that the prime sequence could be inserted at the Bcl I site. To prepare pVAPDBam8 for digestion with Bcl I, which requires the absence of methylated sites within the recognition sequence, the plasmid was transformed into E. coli DH1 (a modification plus and restriction minus strain) and subsequently transformed into E. coli GM-48, (a modification minus and restriction minus). The resulting plasmid, pVAPDBam8-1, was digested with Bcl I. An adapter formed by two kinased, annealed oligonucleotides, ZC525 and ZC526, was ligated with the Bcl I-digested vector. To make this construction two adapters had to blunt-end ligate, then the double adapter had to ligate into the Bcl I cloning site, resulting in a vector having two Eco RI sites flanked by Bcl I sites. This vector was named VAPDR (FIG. 8). To remove the other Eco RI site near the viral origin of replication of this vector, VAPDR was digested with Xho I and Pvu I, and the 3.2 kb fragment, containing the splice sites and polyadenylation sequence, was gel purified. From the similar vector pDX (disclosed in published European patent application EP 276,846 and shown in FIG. 8), a 1.7 kb Xho I-Pvu I fragment, containing the adenovirus origin of replication, SV40 enhancer and adenovirus major late promoter, was gel purified. These two fragments were ligated together with T4 DNA ligase to produce the vector VAPDxR (FIG. 8).

The M13 intergenic region was then added to VAPDxR. Plasmid pVEG was digested with Pvu II and Nar I, blunted with T4 DNA polymerase, then Bam HI linkers were added with T4 DNA ligase. The ligation products were digested with Bam HI, and the DNA fragment was gel purified. VAPDxR was digested to completion with Bam HI and partially digested with Bcl I. The Bcl I-Bam HI fragment containing the adenovirus expression unit was gel purified. The fragments from pVEG and VAPDxR were ligated and transformed into competent LM1035 cells. The construction was screened for correct orientation of the intergenic region. The desired orientation would provide single-stranded DNA of anti-sense polarity in regard to RNA synthesized by the major late promoter. A construct having this configuration was named pDVEG (FIG. 9).

Figure 9:
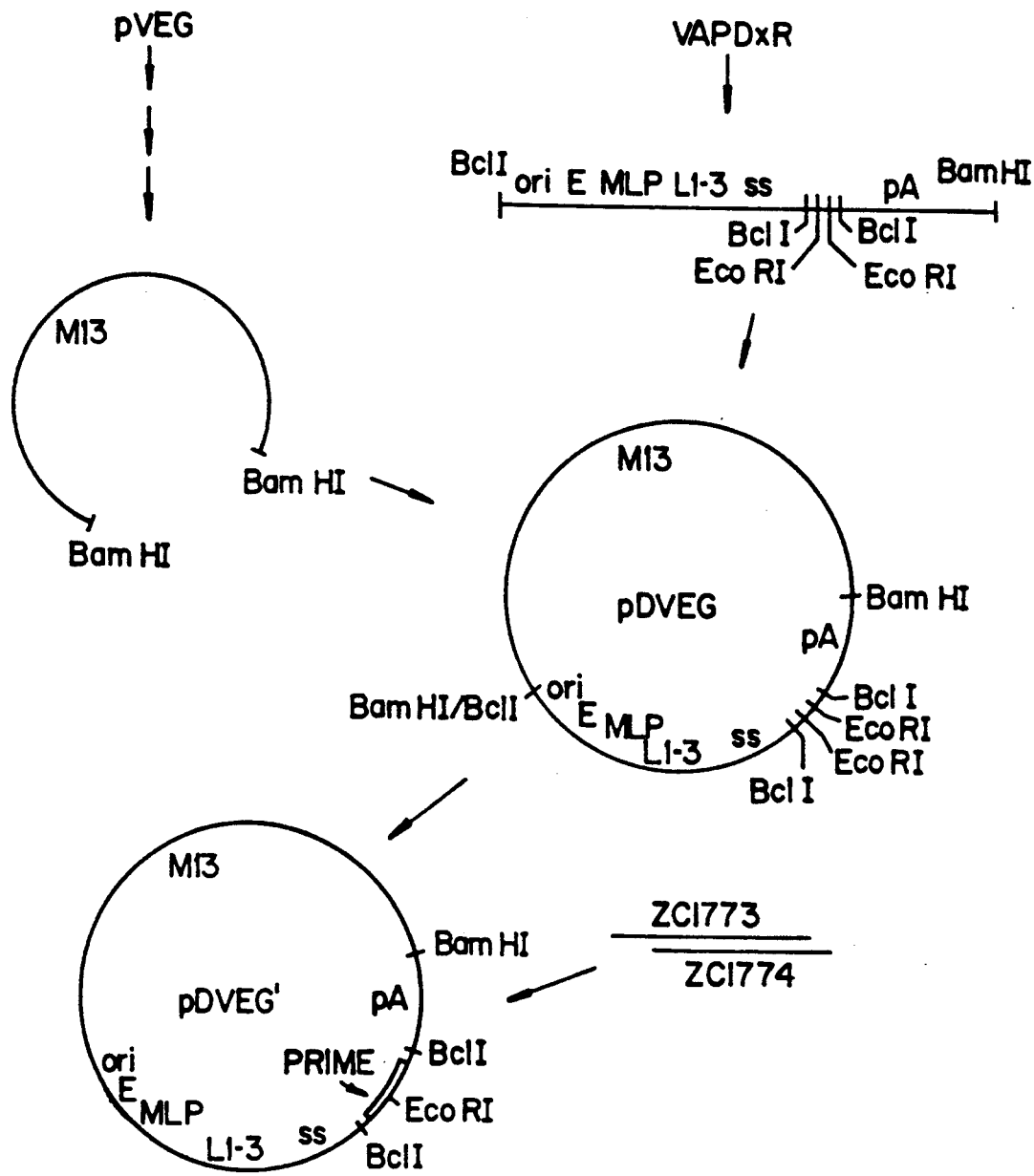

To add the prime sequence to pDVEG, this plasmid was digested with Eco RI (FIG. 9). The prime sequence, constructed by annealing oligonucleotides ZC1773 and ZC1774, was ligated to the Eco RI-digested vector. The ligated DNA was electroporated into DH5αF' ™ cells (obtained from Bethesda Research Laboratories), and the cells were plated. Colony blots were obtained and probed with labeled ZC1773 and ZC1774. Plasmid DNA was prepared from positive colonies and electroporated into XL-I blue cells (obtained from Stratagene Cloning Systems), which contain a tetracycline resistant F' required for M13 infection. Plasmid DNA was prepared from colonies that were resistant to both tetracycline and ampicillin. The region around the Eco RI site was sequenced by double-stranded dideoxy-chain termination DNA sequence analysis. A construct with the correct orientation of the prime sequence was selected and named pDVEG'.

D. Construction of λHG3

Figure 10:
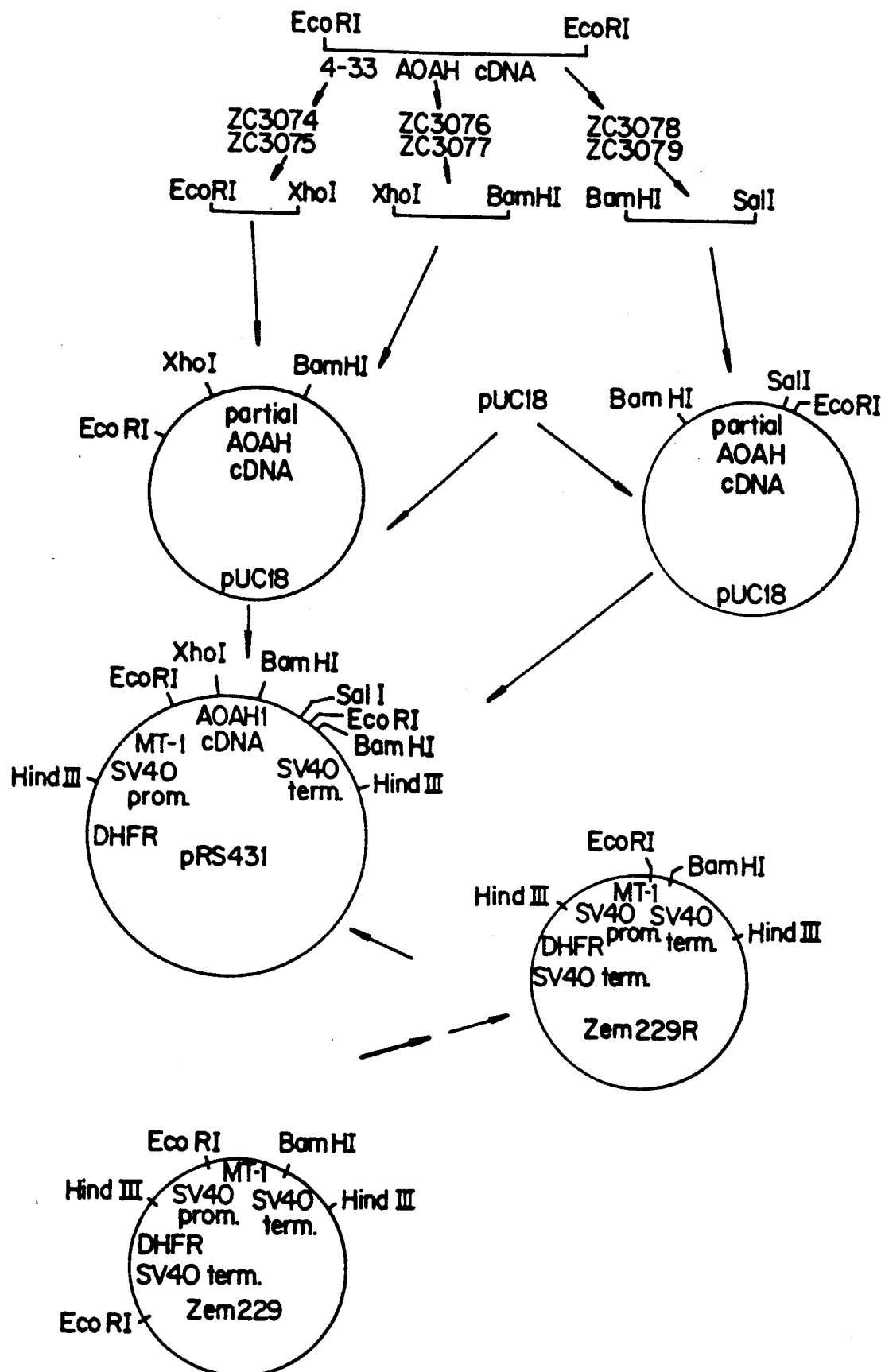
FIG. 10, illustrates the construction of plasmid pRS431. Symbols used are SV40 prom., SV40 promoter; DHFR, the dihydrofolate reductase gene; SV40 term., SV40 polyadenylation sequence; MT-1, metallothionein-1 promoter; 4-33 AOAH cDNA, a fragment derived from the 4-33 AOAH cDNA clone; AOAH1 cDNA, the AOAH1 cDNA.

Plasmid pGEMT was subcloned into λGT11 to facilitate rescue and analysis of cloned DNA sequences as follows. Lambda GT11 DNA was digested with Eco RI and the terminal phosphates were removed by treatment with calf alkaline phosphatase. Plasmid VAPxR (Example ID) was digested with Pst I and was gel-purified. Oligonucleotides ZC554 and ZC553 were designed to form, when annealed, an Eco RI-Pst I adapter with an internal Not I site. Oligonucleotides ZC554 and ZC553 were kinased and annealed and ligated to the linearized VAPDxR vector. The ligation product was gel purified and ligated to the Eco RI-digested lambda GT11. The ligation mixture was packaged and plated on E. coli Y1088 cells. Phage containing the VAPDxR vector were plaque-purified using nick-translated, gel-purified, VAPDxR DNA containing the Eco RI-Pst I adapter. One such isolate was called λGH4. Plasmid pGEMT was inserted into the Not I site of λGH4. Lambda GH4 was linearized by digestion with Not I and treated with calf alkaline phosphatase. Plasmid pGEMT (Example 1A) was linearized by digestion with Not I. The linearized-λGH4 and linearized pGEMT were ligated together, packaged, and plated on *E. coli* Y1088 cells. A clone containing pGEMT was plaque-purifed using nick-translated pGEMT as a probe. The construction was verified by digestion with Not I and was designated λHG3. E. Construction of the Mammalian Expression Vector Zem229R The vector Zem229R was constructed as shown in FIG. 10 from Zem229. Plasmid Zem229 is a pUC18-based expression vector containing a unique Bam HI site for insertion of cloned DNA between the mouse metallothionein-1 promoter and SV40 transcription terminator an an expression unit containing the SV40 early promoter, mouse dihydroflate reductase gene, and SV40 terminator. Zem229 was modified to delete the two Eco RI sites by partial digestion with Eco RI, blunting with DNA polymerase I (Klenow fragment) and dNTPs, and re-ligation. Digestion of the resulting plasmid with Bam HI followed by ligation of the linearized plasmid with Bam HI-Eco RI adapters resulted in a unique Eco RI cloning site. The resultant plasmid was designated Zem229R.

EXAMPLE 2

The Cloning of DNA Sequences Encoding AOAH

A. Amino acid sequence of AOAH

AOAH was purified from DMSO-treated HL-60 cells and used to immunize mice. To induce antibodies, near-pure AOAH was adsorbed to lentil lectin-Sepharose (Pharmacia) and the resulting complex was injected intraperitoneally into mice. After fusion of mouse splenocytes with SP/2 cells, the resulting hybridomas were screened for the production of antibodies to AOAH using an activity depletion assay. One monoclonal antibody that depleted AOAH activity from solution also bound the 50 kD subunit of AOAH on Western blot analysis. The subunits of pure AOAH were then separated by reduction with 2-mercaptoethanol and separated on an SDS-PAGE gel, the 50 kD band was blotted onto a membrane, and the N-terminal amino acid sequence was determined by amino acid microsequence analysis. A 29 amino acid shown in Table 2 was designated the core sequence.

TABLE 2

AOAH Core Sequence

Xxx Asp Ile Xxx Ser Leu Pro Val Leu Ala Lys Ile
Xxx Gln Lys Ile Lys Leu Ala Met Glu Gln Xxx Val
Pro Phe Lys Asp Val

Two synthetic peptides were synthesized from a portion of the core sequence (Cys Ala Ala Ser Leu Pro Val Leu Ala Lys Ile Cys Gln Lys Leu Ala Met Glu Gln and Cys Ala Ala Ser Leu Pro Val Leu Ala Lys Ile Gly Gln Lys Leu Ala Met Glu Gln). Keyhole limpet hemocyanin was coupled to the peptide via the Cys residue of the Cys-Ala-Ala triplet of each peptide using the method essentially described by Green et al., *Cell* 28: 477–487, 1982). Sera from a peptide immunized rabbit also identified a 50 Kd protein by Western analysis.

B. Amplification of the Core Sequence

The DNA sequence encoding the disclosed amino acid sequence was isolated using the method essentially described by Lee et al. (*Science* 239: 1288–1291, 1988). Briefly, 1 μg of HL-60 poly(A)+ RNA, diluted into a total of 5 μl of 5 mM Tris pH 7.0, 0.05 mM EDTA, was heated at 65° C. for 3 minutes, quick chilled in ice water, and reverse transcribed in 10 μl of 50 mM Tris-HCl, pH 8.3, 75 mM KCl, 10 mM DTT, 3 mM MgCl$_2$, 500 μM dNTP, 0.5 μCi/μl α$^{32}$P-dATP containing 6 μg/μl random primer (Pharmacia LKB Biotechnology, Piscataway, N.J.). The reaction was preincubated at 45° C. for 5 minutes and was added to 20 U/μl MMLV(H-) reverse transcriptase (obtained from Bethesda Research Laboratories). Incubation was continued for one hour at 42° C. After incubation, TCA precipitable counts were determined. One microliter of the reaction mixture was added to 500 μl of water containing 100 μg of carrier RNA. The DNA was precipitated with 500 μl 20% TCA. One hundred microliters of this sample was counted directly to determine total counts in reaction. The remainder of the TCA sample was collected on a glass filter and washed with 10% TCA and counted. The synthesis yielded 250 ng of DNA.

Ninety microliters of 1 mM EDTA, 0.2N KOH were added to the remainder of the reaction sample. The sample was incubated for 15 minutes at 65° C. to hydrolyze the RNA. The primer and small molecules were removed by an alkaline Sepharose 6B column chromatography, poured in a 1 ml disposable pipet, in 50 mM KOH, 0.1 mM EDTA. (The column was washed with 50 column volumes of buffer prior to use.) The cDNA in the void volume was collected and ethanol precipitated after the addition of 5 μg of carrier oyster glycogen. The random-primed cDNA was resuspended in 50 μl of 10 μm Tris pH 7.4, 10 mM NaCl, and 0.1 mM EDTA.

Degenerate oligonucleotides were designed and synthesized to correspond to the terminal portions of the disclosed sequence and in addition contained sequences encoding terminal Eco RI sites to facilitate subcloning. The sense core primer family, ZC2388, (Table 3) and the antisense core primer family, ZC2295, (Table 3) were used to amplify the cDNA using the method essentially described by Lee et al. (ibid.). Forty-two nanograms of random-primed cDNA was added to a reaction containing 1X PCR buffer (perkin Elmer Cetus, Norwalk), 200 μM dNYTPs, 400 pmoles of ZC2388, 400 pmoles of ZC2295 and 2.5 U of Taq I in a 100 μl reaction. A mineral oil overlay was added to the reaction mixture, and the PCR reaction was carried out under the conditions shown in Table 4.

TABLE 3

Core Primer and Probe Families

ZC2388 - Sense core primer family
23-mer, family of 256.
```
Eco RI      A   A   A
            CC  C   C   A
         TCAGAATTCGTGTTGGCGAAGAT
             T   T   T
```

ZC2295 - Antisense core primer family
26-mer, family of 128.
```
Eco RI                  A   A
                    G T G C   C
         GATGAATTCACATCCTTAAAGGGGAC
                        T   T
```

ZC2389 - 17-mer probe family of 128
```
         A   A
      GT C   C           A   A
      AAACTGGCGATGGAGCAG
          T   T
```

ZC2298 - 26-mer I-probe family of 16

TABLE 3-continued

Core Primer and Probe Families

|  |  |  |  |
|---|---|---|---|
| A | A | A | A |
| CAGAAGATIAAGITIGCIATGGAGCA | | | |

TABLE 4

Conditions for Polymerase Chain Reaction Amplification of the AOAH Core Sequence

| | |
|---|---|
| 94° C. for 3 minutes | 3 cycles |
| 30° C. for 2 minutes | |
| 72° C. for 4 minutes | |
| 94° C. for 2 minutes | 40 cycles |
| 55° C. for 2 minutes | |
| 72° C. for 4 minutes | |

After the last cycle, the samples were extracted with 100 μl chloroform to remove oil overlay. Five micrograms of oyster glycogen and 4 μl 0.5M EDTA were added, and the samples were phenol-chloroform extracted. The amplified DNA was ethanol precipitated and resuspended in 60 μl of water.

The resuspended amplified DNA was cloned into the Eco RI site of a λHG-3. To accomplish this, the amplified DNA was digested with Eco RI and the digest was run on a 4% NuSieve agarose TBE gel. Ultraviolet illumination revealed a faint band at about 71 nucleotides. This band was electrophoresed onto NA-45 paper (Schueller and Schneller) and was eluted by incubation at 65° C. for 20 minutes in 400 μl of 1.5M NaCl, 10 mM Tris pH 7.4, and 0.1 mM EDTA. After the addition of 5 μg of oyster glycogen, the sample was phenol-chloroform extracted three-times and ethanol precipitated. The DNA was resuspended in 10 μl water.

The Eco RI-digested DNA was ligated with λHG-3, which had been digested with Eco RI and dephosphorylated with calf alkaline phosphatase. The ligation mixture was incubated at room temperature for 2 hours. Gigapack Plus packaging mix (Stratagene Cloning Systems, Inc., La Jolla, Calif.) was added and the incubation was continued at room temperature for 2 hours. After incubation, 225 μl of SM buffer (Maniatis et al., ibid.) was added, and the solution was vortexed gently. Thirty microliters of chloroform was added, and the sample was gently vortexed. After a 2 minute centrifugation, the aqueous phase was diluted 1/100 and 10 μl was plated on *E. coli* Y1088 cells.

Plaque lifts were prepared using the method essentially described by Benton and Davis (*Science* 196: 1801, 1977). Two oligonucleotide families of probes were designed that would identify the sequence between the core PCR primers. The probe families, ZC2389 and ZC2298, consisted of a 17 mer of a family of 128 oligonucleotides and a 26 mer of a family of 16 oligonucleotides with inosines in the most ambiguous positions, respectively (Table 3). These oligonucleotides were kinased and duplicate plaque lifts were probed with each probe family. Six positive plaques were chosen for further analysis.

Plate lysates were prepared from each isolate and lambda DNA was obtained by the method essentially described by Helms et al. (*DNA* 4: 39, 1985). Plasmids residing in the λ vectors were released with the method called "λ-pop" essentially as described by Hagen (ibid.). Briefly, the λ isolates were digested with Not I, which liberates the complete pGEMT plasmid. The Not I-digested DNA was ligated for 5 hours at room temperature followed by heat denaturation of the ligase at 65° C. for 10 minutes. The ligation mixtures were phenol-chloroform extracted, ethanol precipitated, and the DNA was electroporated into *E. coli*. Plasmid DNA was prepared from the transformants using the method essentially described by Holmes and Quigley (*Anal. Biochem.* 114: 193, 1981). The DNA sequence of the core fragment was determined by dideoxy-chain termination method on double stranded plasmid DNA, using a vector sequence primer. The translation of the DNA sequence showed that the deduced amino acid sequence (Table 5) was identical to the core AOAH amino acid sequence and supplied the unknown amino acids at positions 13 and 23 (Table 2) with Cys and Ser, respectively.

TABLE 5

AOAH Core Sequence Derived from PCR Amplification and Deduced Amino Acid Sequence

| | Val | Leu | Ala | Lys | Ile | Cys | Gln | Lys | Ile | Lys | Leu | Ala | Met |
|---|---|---|---|---|---|---|---|---|---|---|---|---|---|
| 5' | GTT | TTG | GCC | AAG | ATC | TGC | CAG | AAA | ATT | AAA | TTA | GCT | ATG |
| | 1 | | | 10 | | | 20 | | | 30 | | | |
| | Glu | Gln | Ser | Val | Pro | Phe | Lys | Asp | Val | | | | |
| | GAA | CAG | TCT | GTG | CCA | TTC | AAA | GAT | GT 3' | | | | |
| | 40 | | | 50 | | | 60 | | | | | | |

C. Isolation of Partial cDNA Clones

Partial AOAH cDNA clones were obtained from a cDNA library prepared from a DMSO-stimulated HL-60 cell RNA. RNA template for this library was prepared using the method essentially described by Chirgwin et al. (*Biochemistry* 18: 5294–5299, 1979). Poly(A)+ RNA was selected by two passages over an oligo-d(T) column. A lambda gt11 cDNA library was prepared from this RNA using an Invitrogen Inc. "Lambda Librarian" cDNA kit and a modification of the manufacturer's instructions. Briefly, double-stranded cDNA was synthesized using five micrograms of twice-selected poly(A)+ RNA and using the manufacturer's prescribed directions. The cDNA was blunted with T4 DNA polymerase, Eco RI adapters were added, and the cDNA was phosphorylated as described by the manufacturer. Following the phosphorylation, the cDNA was phenolchloroform extracted two times. The cDNA was size-selected and the unincorporated primers were removed by chromatography on a 1.1 ml Sepharose 6B-CL column equilibrated with 10 mM Tris pH 7.4, 150 mM NaCl, and 0.1 mM EDTA. Fractions of the void volume containing the cDNA were pooled and the cDNA was ethanol precipitated. The cDNA was ligated to Eco RI-digested dephosphorylated lambda gt11 (Clontech Inc.). The DNA was packaged using Gigapack Plus packaging mix (Stratagene Cloning Systems) and plated on *E. coli* Y1088 cells. A plate lysate library was prepared which contained 13.3 million independent isolates with a background of 1%. The actin positivity of the library was 0.34% (Hagen et al., *BioTechniques*, 6: 340, 1988). The plate lysate library was stored at 4° C. over chloroform.

To screen the library for AOAH cDNA clones, duplicate filter lifts were prepared from 20–150 mm plates containing 7.2 million phage. The filters were probed with radiolabeled ZC2465, which was designed from the core sequence. The probe was hybridized at 37° C. in 20% Ullrich's hybridization buffer (Ullrich et al., EMBO J.3: 361–364, 1984) and washed in 2X SSC (Maniatis et al, ibid.) at 50° C. Two potential positives, which appeared on duplicate lifts, were plaque purified and were designated clone 1.1 and clone 2.1. The cDNA inserts from these lambda clones were subcloned into pVEGT' and sequenced by double-stranded dideoxy-chain termination DNA sequence analysis. Sequence analysis of the cDNA inserts of clones 1.1 and 2.1 showed that the two clones were overlapping but incomplete and contained different sequences near the 5' ends and different coding capacities.

D. Preparation of 3' Template cDNA For Amplification of 3' AOAH coding sequences Complementary DNA was synthesized from U-937 poly(A)+ RNA utilizing ZC2487 (Table 1), which was designed to encode a oligo-d(T), Xho I, Sal I and Cla I primer. One microgram of U-937 poly(A)+-enriched RNA in 2 μl water was mixed with 2 μl 10 mM Tris, pH 7.0, 0.1 mM EDTA, heated at 65° C. for 3 minutes and quick-chilled in ice water. Two microliters of 5× buffer (50 mM Tris-HCl, pH 8.3, 75 mM KCl, 10 mM DTT, 3 mM MgCl$_2$) was mixed with 0.5 μl 10 mM dNTP, 1 μl of 5 pmole/μl ZC2487 for, 1.0 μl of water, and 0.5 μl 5 μCi/μl α$^{32}$P-dATP. The RNA solution was added to the reaction mixture and preincubated at 45° C. for 5 minutes. One microliter of 200 unit/μl MMLV(H-) reverse transcriptase was added after the preincubation, and the sample was incubated for 1 hour at 45° C. After incubation, 1 μl of 0.5M EDTA and 1 μl of 5N KOH were added to the samples, and the RNA was hydrolyzed by incubation at 65° C. for 15 minutes.

E. Preparation of 5' Template cDNA For Amplification of 5' AOAH coding sequences Complementary DNA was prepared to the 5' portion of the AOAH coding sequence using essentially the method of Frohman et al. (ibid.). Complementary DNA was synthesized from U-937 poly(A)+ RNA utilizing the oligonucleotide primer ZC2487 encoding an antisense sequence corresponding to nucleotides 8 to 40 of the core sequence shown in Table 4. One microgram of poly(A)+-enriched RNA in 2 μl of water was mixed with 2 μl 10 mM Tris, pH 7.0+0.1 mM EDTA, heated at 65° C. for 3 minutes and quick-chilled in ice water. Two microliters of 5× buffer was mixed with 0.5 μl 10 mM dNTP, 1 μl of 5 pmole/μl ZC2634, 1.0 μl of water, and 0.5 μl 5 μCi/μl α$^{32}$P-dATP. The RNA solution was added to the reaction mixture and preincubated at 45° C. for 5 minutes. One microliter of 200 unit/μl MMLV(H-) reverse transcriptase was added after the preincuabtion, and the sample was incubated for one hour at 45° C. After incubation, 1 μl of 0.25M EDTA and 290 μl of 0.05N KOH were added to the samples, and the RNA was hydrolyzed by incubation at 65° C. for 15 minutes.

The primers were removed from the cDNA sample by ultrafiltration through a Centricon Special YM-100 ultrafiltration unit in the presence of 50 mM KOH and 0.1 mM EDTA using conditions described by the manufacturer. After filtration the DNA was ethanol precipitated with the aid of 5 μg of oyster glycogen. The DNA was resuspended in 5.7 μl in H$_2$O. The DNA was G-tailed by mixing the 5.7 μl of DNA with 0.3 μl of water, 2 μl of 5× TdT buffer (100 mM potassium cacodylate, pH 7.2, 2 mM CaCl$_2$, 0.2 mM DTT, 1 mg/ml BSA) and 1 μl of 1 mM dGTP. After a pre-incubation of 5 minutes at 15° C., 38.5 units of terminal deoxynucleotidyl transferase (obtained from Collaborative Research) was added to the reaction mixture. The incubation was continued for an additional three minutes, and 90 μl of 200 mM NaCl+20 mM EDTA+10 mM Tris pH 8.3 was added to stop the reaction. The DNA was ethanol precipitated, washed with ethanol, and resuspended in 20 μl of water.

For second strand synthesis of the tailed cDNA, 20 μl of the G-tailed DNA was mixed with 47 μl of water, 10 μl of 10× PCR buffer(—MgCl$_2$) (500 mM NaCl, 100 mM Tris-Cl, pH 8.3 (at room temperature), 0.1% gelatin), 16 μl of 1.25 mM dNTPs, 4 μl 50 mM MgCl$_2$, 5 pmole of ZC2488, which encodes a poly d(C), Xho I, Sal I, Cla I primer. After the sample was preincubated at 94° C. for 5 minutes, 5 units of Taq I were added followed by an oil overlay. The incubation was continued at 40° C. for 5 minutes, and 72° C. for 15 minutes. One microliter of 250 mM EDTA was added to stop the reaction, and the sample was chloroform extracted to remove the oil overlay. Five micrograms of oyster glycogen was added and the sample was ethanol precipitated.

F. Enrichment of 5' and 3' Template cDNAs

The 5' and 3' template cDNAs were fractionated by alkaline gel electrophoresis and the DNA from each gel fraction was PCR amplified to identify the gel fragments containing amplifiable AOAH coding sequences. An equal volume of 2× alkaline loading dye (60 mM NaOH, 4 mM EDTA, 20% glycerol, and 60% by volume bromcresol purple saturated with water) was added to the 3' template cDNA. Half of the DNA in from the 5' template cDNA was similarly prepared for electrophoresis and the DNA of the samples were fractionated on a 1% low melt alkaline agarose gel (1% low-melt agarose in 30 mM NaOH+2 mM EDTA). After electrophoresis, the agarose gel was cut into 12–0.5 cm fragments, representing DNA from 7,000 to 700 nucleotides for the 3' cDNA and in 8–1 cm fragments for the 5' cDNA. The gel fragments were melted at 65° C. The melted gel fragments containing 3' template cDNA were diluted with 400 μl water for the 3' cDNA. The melted gel fragments containing 5' cDNA were used directly.

PCR amplification was performed with gel fragments 1 to 12 for the 3' cDNA and gel fragments 2 to 6 for the 5' cDNA essentially as described by Frohman et al. (ibid.). Ten microliters each of the 3' template cDNA from fragments 1–12 was mixed with 10 μl 10×PCR Buffer(—MgCl$_2$), 57 μl of water, 16 μl of 1.23 mM dNTPs, 2 μl 50 mM MgCl$_2$, 2 μl of 5 pmol/μl ZC2469 (encoding nucleotides 1–22 of the core sequence) and 2 μl of 5 pmol/μl ZC2489 (encoding the Xho I-Sal I-Cla I adaptor sequence). One microliter each of the 5' template cDNA from fragments 2–6 were mixed with 10 μl 10× PCR Buffer(—MgCl$_2$), 66 μl of water, 16 μl of 1.25 mM dNTPs, 2 μl of 50 mM MgCl$_2$, 2 μl of 5 pmol/μl ZC2634 and 2 μl of 5 pmol/μl of ZC2633. Five units of Taq I DNA polymerase were added to each mixture during the first 94° C. denaturation period, followed by a mineral oil overlay, and the mixtures were amplified according to the conditions set forth in Table 6.

Table 6

Conditions for the Amplification of 3' DNA Sequences
TWO CYCLE:
94° C. for 1 minute
50° C. for 2 minutes
72° C. for 3 minutes
FORTY CYCLES:
94° C. for 1 minute
65° C. for 2 minutes
72° C. for 3 minutes Conditions for the Amplification of 5' DNA Sequences
FORTY CYCLES:
94° C. for 2 minutes
72° C. for 4 minutes
ONE CYCLE:
72° C. for 4 minutes Following amplification, 10 µl each of the PCR reactions was electrophoresed on a 0.8% agarose gel after the addition of 2 µl of 5× loading dye (0.45 M Tris, 0.45 M boric acid, 0.01 M EDTA, 50% glycerol, 0.13% xylene cyanol, and 0.13% bromphenol blue). The gels were analyzed by visualization with ethidium bromide intercalation and UV-illumination followed by Southern blot analysis. Analysis of 3' PCR products showed a few minor bands by staining with ethidium bromide, but none of them proved to be the DNA band of interest as revealed by Southern blot analysis using a kinased antisense probe (ZC2470). The Southern blot hybridization pattern showed that the largest hybridizable band was at approximately 1500 nucleotides. This 1500 nucleotide band was most prominent from gel fragment #3, which contained template cDNA to 3000 nucleotides. The DNA eluted from fragment #3 was used in all additional experiments to obtain the 3' AOAH coding sequences.

Analysis of the PCR products produced from the 5' PCR product did not reveal any DNA bands by ethidium bromide staining. Southern analysis with a random-primed 5' Eco RI-Xba I fragment of AOAH cDNA clone 1.1 revealed a hybridizable band at about 700 nucleotides from gel fragment #4.

Amplification of DNA from fragment #3 using ZC2469 and ZC2489 occasionally produced small quantities of the desirable DNA fragments; however smaller hybridizable bands were often the sole PCR product. Similarly, it was difficult to reproducibly obtain the desired 5' AOAH PCR product. Finally, the PCR products would not clone via the restriction sites which were contained in the primers. Therefore the "Prime" sequence (described by Hagen in a co-pending commonly assigned U.S. patent application Ser. No. 07/320,191, which is incorporated by reference herein) was added to the primers and to facilitate the cloning of the PCR products after amplification.

G. Amplification of 5' and 3' AOAH Coding Sequence

The DNA from fragment #3 was amplified using oligonucleotides ZC2631 and ZC2632. The 3' reaction mixture was prepared as follows. One microliter of DNA from fragment #3 was mixed with 10 µl 10× PCR Buffer(—MgCl$_2$), 76 µl of water, 16 µl of 1.25 mM dNTPs, 2 µl of 50 mM MgCl$_2$, 2 µl each of 5 pmol/µl ZC2631 (the 5'prime-sense primer) and 5 pmol/µl ZC2632 encoding a prime sequence joined to the 3' end of the adapter sequence).

The DNA from fragment #4 was amplified using oligonucleotides ZC2633 and ZC2634. The 5' reaction mixture was prepared as follows. One microliter of gel fragment #4 was mixed with 10 µl 10× PCR Buffer-(—MgCl$_2$),76 µl of water, 16 µl of 1.25 mM dNTPs, 2 µl of 50 mM MgCl$_2$2 µl each of 5 pmol/µl ZC2633 (the 5' prime-adapter primer) and 5 pmol/µl ZC2634 (the 3' prime-antisense primer). Five units of Taq I DNA polymerase and a mineral oil overlay were added to the sample during the 94° C. denaturation step of the first cycle. The reaction mixtures were amplified according the conditions set forth in Table 7.

Table 7

Conditions for Amplifying 5' and 3' Sequences Using Prime-primers

FORTY CYCLES:
94° C. for 2 minutes
72° C. for 4 minutes
ONE CYCLE:
72° C. for 4 minutes After amplification, 10 µl of each sample was analyzed by agarose gel electrophoresis. Analysis of the gel revealed a minor band at 1500 nucleotides and major band at 800 for the 3' product. The amplification of the 5' DNA did not produce sufficient amounts of 5' PCR product after one round of RACE to clone the DNA, To produce enough 5' PCR product for subcloning, 10 µl of DNA from the first amplification reaction was reamplified for 40 cycles, using the conditions set forth in Table 4. After amplification, all of the samples were chloroform, extracted followed by phenol/chloroform extraction. The DNAs were filtered on a Centricon Special YM100 microfiltration unit followed by ethanol precipitation with oyster glycogen as carrier. The PCR products were resuspended in water.

The PCR products were subcloned by treating the double-stranded DNA with T4 DNA polymerase in the presence of dATP to produce single-stranded prime sequences complementary to prime sequences present in the vector pVEGT'. The PCR product were each mixed with 1 µl of 10× T4 buffer, 1 µl of 1 mM dATP, 1 µl of 50 mM DTT and 1 unit of T4 DNA polymerase. The reactions were incubated 1 hour at 15° C. The polymerase was heat denatured at 65° C. for 15 minutes.

The T4 DNA polymerase cut-back PCR products were electrophoresed in a 0.8% low melt agarose gel, and the 1500 bp and 800 bp bands were gel-purified. The cut-back DNA was ligated with the cut-back pVEGT'. Plasmid DNA was prepared from the transformants using the method essentially described by Holmes and Quigley (ibid.). Analysis of the plasmid DNA by Eco RI restriction analysis revealed 6 clones containing the 1500 bp 3' cDNA and 5 clones containing the 800 bp 5' cDNA. DNA sequence analysis of these clones confirmed that the clones contained DNA sequences that overlapped the core sequence and comparison with the DNA sequence of the 1.1 and 1.2 cDNA clones established a full length sequence of 2290 bp.

H. Amplification of Full Length AOAH cDNA

Full length cDNAs were generated by PCR amplification from the DNA from fragment #3 using oligonucleotide primers designed from sequences from the 5' and 3' clones. Oligonucleotides ZC2703, encoding the prime sequence joined to the 5' end of the sequence of nucleotides 38 to 61 of FIG. 1, and ZC2704, encoding the prime sequence joined to the 3' end of an antisense sequence corresponding to nucleotides 2175 to 2198 of FIG. 1, were used in two separate series of PCR reactions to obtain two independently derived AOAH clones. In one reaction, 1 μl of fragment #3 was amplified in a 100 μl volume PCR reaction (1X DNA polymerase buffer (Promega Biotech), 200 μM dNTP, 0.25 μM of each primer, 22.5 units/ml of Promega Biotech Taq 1 DNA polymerase) under the conditions set forth in Table 8. Ten microliters of the above-described reaction was subjected to a second round of amplification under conditions identical to those described above. The resulting PCR product was designated as C. In a second reaction, 10 μl of fragment #3 was used as the starting template for 2 rounds of 30 cycles of PCR amplification identical to those described above except that the Promega Biotech Taq 1 DNA polymerase was used at a concentration of 45 units/ml. The resulting PCR product was designated as 4.

Table 8
Conditions for Amplifying Full-length AOAH cDNA
THIRTY CYCLES:
94° C. for 2 minutes
72° C. for 4 minutes ONE CYCLE:
72° C. for 4 minutes
cool to room temperature After the two rounds of PCR as described above, samples C and 4 were extracted with chloroform to remove the oil overlay. One hundred microliters of 20 mM Tris pH 8.3+200 mM NaCl+20 mM EDTA was added, and the solution was extracted with phenol-chloroform. The primers were separated from the PCR products by ultrafiltration with Amicon Centricon Special YM100 ultrafiltration device as described by the manufacture using water as the eluate. Five micrograms of oyster glycogen was added and the DNA was ethanol precipitated. The PCR products and the Eco RI-linearized pDVEG (Example IC) were exonucleased using T4 DNA polymerase to expose the prime sequences. As described in Example 2G, the PCR products were treated in a 10 μl T4 DNA polymerase reaction. After 1 hour, the samples were incubated for 15 minutes at 65° C. to inactivate the polymerase. The DNA was electrophoresed on a 0.8% low melt agarose gel, and the amplified DNA was gel-purified. The cut-back PCR products were each ligated to the cut-back pDVEG.

The DNA was electroporated into E. coli DH5αF ™ (Bethesda Research Labs) and plated. Plasmid DNA was prepared, and the DNA analyzed by restriction endonuclease analysis. One clone from C and one clone from 4 were chosen and designated C/26 and 4-33. Clones C/26 and 4-33 were sequenced by the dideoxy chain-termination method. The sequences of C/26 and 4-33 are shown in FIGS. 1 and 2, respectively.

I. Construction of a Consensus DNA Sequence.

Because PCR synthesis can incorporate mutations into amplified DNA, depending on the number of cycles and conditions of DNA synthesis, it was necessary to be rigorous about establishing a consensus sequence. By comparing the sequences of the two full length PCR clones, the 5' AOAH PCR products, two 3' AOAH products, and the two partial cDNA clones, a consensus AOAH cDNA sequence was established as shown in FIG. 3. A comparison of the sequences showed that clone 4-33 (FIG. 2) had three PCR-induced mutations resulting in three amino acid changes and clone C/26 (FIG. 1) had nine PCR-induced mutations resulting in seven amino acid changes.

A consensus DNA sequence encoding AOAH was constructed from the AOAH clone 4-33 (FIG. 1) which has the fewest (three) PCR-induced mutations: A to G at position 636, changing Asparagine 117 to Serine; A to G at position 1479, changing Glutamine 398 to Arginine; T to C at position 1539, changing Leucine 418 to Serine. These lesions are corrected as follows to construct a consensus DNA sequence termed AOAH1 (FIG. 4).

Standard protocols for PCR template preparation and PCR reaction conditions were followed (Innis, Gelfand, Sninsky, and White, T. J., eds. *PCR Protocols*, Academic Press, 1990). Specifically, the PCR template was a 2.2 kb Eco RI fragment of clone Zem229R-4-33 (Example 3). As shown in FIG. 10, Oligonucleotides ZC3074, a sense primer which inserts a mammalian consensus ribosome binding site (encoding the nucleotide sequence CCACC) just upstream of the initiation Methionine, preceded by Sal I and Eco RI sites and encodes nucleotides 252 to 269 of FIG. 1, and ZC3075, an antisense primer which corresponds to nucleotides 576 to 596 and inserts an Xho I site at position 584, were synthesized and used to amplify 4-33 DNA. After amplification, the DNA was digested with Eco RI and Xho I to isolate a 346 bp Eco RI-Xho I fragment encoding nucleotides 2-348 of FIG. 4.

The mutations at positions 601 and 1444 of clone 4-33 (FIG. 1) were corrrected by PCR amplification using oligonucleotides ZC3076, a sense oligonucleotide primer corresponding to nucleotides 576 to 607 of FIG. 1 which creates an Xho I site by making a silent mutation at position 584 and which corrects the mutation at position 601, and ZC3077, an antisense oligonucleotide primer corresponding to nucleotides of FIG. 1 which creates a Bam HI site at position 1481 by making silent mutations at positions 1481, 1482 and 1483 and corrects the mutation at position 1444. As shown in FIG. 10, the 2.2 kb Eco RI fragment of 4-33 DNA was subjected to PCR amplification using oligonucleotides ZC3076 and 3077. The amplified DNA was digested with Xho I and Bam HI to isolate an 897 bp Xho I-Bam HI fragment encoding nucleotides 349 to 1245 of FIG. 4.

The mutation at position 1504 of clone 4-33 was corrected by PCR amplification. As shown in FIG. 10, oligonucleotides ZC3078, a sense primer corresponding to nucleotides 1473 to 1511 of FIG. 1 which inserts the same Bam HI site as ZC3077 and corrects the mutation at position 1504 of FIG. 1, and ZC3079, an antisense primer which corresponds to nucleotides 1967 to 1999 of FIG. 1 and which inserts Sal I and Eco RI sites immediately downstream of the stop codon were used to amplify 4-33 DNA. The amplified DNA was digested with Bam HI and Sal I to isolate a 507 nucleotide Bam HI-Sal I fragment encoding nucleotides 1246 to 1752 of FIG. 4.

The PCR products were subcloned into pUC18 as shown in FIG. 10. The Eco RI-Xho I fragment, comprising the 5' sequence of AOAH encoding nucleotides 2 to 348 of FIG. 4, and the Xho I-Bam HI fragment, comprising an AOAH sequence corresponding to nucleotides 349 to 1245 of FIG. 4 having the corrected sequence at positions 367 and 1210 (corresponding to positions 602 and 1444 of FIG. 1, respectively), were ligated together with Eco RI-Bam HI-digested pUC18. The resulting plasmids were confirmed by sequence analysis. A clone having the correct insert was digested with Eco RI and Bam HI to isolate the Eco RI-Bam HI fragment, comprising the AOAH sequence corresponding to positions 2 to 1245 of FIG. 4. In a separate reaction, the Bam HI-Sal I fragment, comprising an AOAH sequence corresponding to nucleotides 1246 to 1752 of FIG. 4 having the corrected sequence at position 1270 (corresponding to position 1504 of FIG. 1) was ligated with Bam HI-Sal I-digested pUC18.

After the AOAH-specific portions of the above ligation were confirmed by sequence analysis, the partial AOAH cDNA were reassembled in a mammalian expression vector as shown in FIG. 10. The Bam HI-Eco RI fragment, comprising an AOAH sequence corresponding to nucleotides 1246 to 1752 of FIG. 4, was isolated from a plasmid clone having the correct insert. The Eco RI-Bam HI fragment and the Bam HI-Eco RI fragment were joined with Eco RI-linearized Zem229R by ligation. The resulting plasmid containing the AOAHI sequence from FIG. 4 was designated pRS431 (FIG. 10).

EXAMPLE 3

Expression of AOAH in Cultured Mammalian Cells

A. Construction of Mammalian Expression Vectors

The AOAH cDNAs contained in plasmids C/26 and 4-33 were subcloned into the mammalian expression vector Zem229R. Plasmids C/26 and 4-33 were digested with Eco RI to isolate the AOAH cDNA. Plasmid Zem229R was linearized by digestion with Eco RI and treated with calf alkaline phosphatase to prevent recircularization. The cDNAs from C/26 and 4-33 were each ligated with the linearized Zem229R. Plasmid clones having the C/26 and 4-33 inserts in the correct orientation relative to the promoter were designated Zem229R-C/26 and Zem229R-4-33, respectively. Plasmid Zem229R-C/26 and Zem229R-4-33 have been deposited as *E. Coli* transformants with the American Type Culture Collection (Rockville, Md.).

B. Expression of AOAH cDNAs in Mammalian Cells

Plasmids Zem229R-C/26 and Zem229R-4-33 were transfected into BHK 570 cells (deposited with the American Type Culture Collection under accession number 10314) using the calcium phosphate-mediated transfection method essentially described by Chen et al. (*BioTechniques* 6: 632, 1988). After the transfected cells were grown for three days, 10 ml of media was taken for each transfection and from a negative control and stored at 4° C. The transfections and a negative control were trypsinized and resuspended in 10 ml of media and counted. The cells were centrifuged and the media was discarded. The cell pellet was resuspended in 1× PBS (phosphate-buffered saline, Sigma Chemical Co., St. Louis, Mo.)+0.1% Triton X-100+1 mM PMSF to a concentration of 1×10⁶ cells/100 μl. The resuspended cells were lysed for 10 minutes at room temperature and the lysates were centrifuged at 100,000 rpm in a microfuge for 10 minutes at 4° C. The supernatants were removed and placed on ice.

The duplicate spent media samples and duplicate lysate supernatants were assayed for AOAH activity using the method essentially described by Munford and Hall (*Science* 234: 203–205, 1986). Briefly, 100 μl of media or lysate was added to 400 μl of reaction buffer, pH 4.8 (1.25 mg/ml BSA, 0.625% Triton X-100, 187.5 mM NaCl, 6.25 mM $CaCl_2 \cdot H_2O$, mM Tris-Base, 12,5 mM citric acid) containing 1 μl $^{14}C/^{3}H$-LPS Substrate. The reaction mixtures were incubated for approximately 16 hours at 37° C. After incubation, 1 ml of cold 100% ethanol was added and the mixtures were vortexed and chilled on ice for 45 minutes. The samples were centrifuged for 10 minutes at 4° C. at 10,000 rpm. One milliliter of supernatant from each sample was removed and lyophilized in a glass scintillation vial. Five milliliters of Optifluor scintillation fluid (Packard Instrument Co, Downers Grove, Ill.) was added and the samples were counted for 2 minutes on the tritium channel. The results of the assay are shown in Table. 9.

TABLE 9

| AOAH Activity Assay Results | |
|---|---|
| Sample | Counts |
| Positive Control: | 2799 |
| 1 μl 1:100 dilution of purified AOAH | 2984 |
| Negative Control: | 184 |
| reaction buffer | 153 |
| Negative Control: | 241 |
| BHK 570 cell media | 175 |
| Negative Control: | 184 |
| BHK 570 cells | 181 |
| Zem229R-C/26 media | 193 |
|  | 039 |
| Zem229R-C/26 cells | 450 |
|  | 477 |
| Zem229R-4-33 media | 193 |
|  | 214 |
| Zem229R-4-33 cells | 2866 |
|  | 3091 |

As shown in Table 9, the Zem229R-C/26 and Zem229R-4-33 transfectants contained AOAH activity with Zem229R-C/26 transformants having only approximately 18% of the activity of the Zem229R-4-33 transfectants.

Plasmids Zem229R-4-33 and pRS431 were each transfected into BHK 570 cells by calcium phosphate precipitation as described above. Transfectants were lysed and the lysates were assayed for activity essentially as described above. As shown in Table 10, both the Zem229R-4-33 and the pRS431 transfectants had AOAH activity with pRS431 transfectants, which express the consensus AOAHI sequence of FIG. 4, having more than twice the activity as the Zem229R-4-33 transfectants.

TABLE 10

| AOAH Activity Assay Results | |
|---|---|
| Sample | $H^3$-fatty acid released, dpm/mg cell protein |
| Zem229R-4-33 cells | 2038 |
| pRS431 cells | 4973 |

The deacylation of LPS using the recombinant AOAH purified from Zem229R-4-33 transfectants was measured as the maximal percent of triturated fatty acids released from AOAH-treated, labeled LPS using a protocol essentially as described in U.S. Pat. No. 4,929,604, which is incorporated herein by reference.

Biosynthetically labeled LPS was deacylated with enzyme contained in an extract of Zem299-4-33 transfected cells. An extract of cells that did not contain the transfected DNA was incubated with the LPS under identical conditions as a control. After incubation, the reaction mixtures were extracted with chloroform/methanol and the chloroform extracts (which contained the $^3$H-fatty acids) were counted. Calculation of the percent of the $^3$H radioactivity that was released from the LPS by the extract of Zem99-4-33 transfected cells indicated that approximately 27% of the fatty acids were removed; the extract of untransfected cells removed less than 2%. This level of deacylation is consistent with the fact that only one third of the fatty acyl chains in LPS are susceptible to cleavage by AOAH. In addition, in the same experiment a large excess of purified neutrophil AOAH released 27% of the triturated fatty acids from the LPS.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated DNA molecule comprising a DNA segment encoding an avian or mammalian acyloxyacyl hydrolase free of other genes with which it is associated in the genome wherein said acyloxyacyl hydrolase comprises a small subunit and a large subunit.

2. An isolated cDNA encoding an avian or mammalian acyloxyacyl hydrolase wherein said acyloxyacyl hydrolase comprises a small subunit and a large subunit.

3. A DNA module according to claim 1 or 2 wherein said DNA sequence comprises the DNA sequence of FIG. 1 from nucleotide 354 to nucleotide 1976, the DNA sequence of FIG. 2 from nucleotide 354 to nucleotide 1976, the DNA sequence of FIG. 3 from nucleotide 389 to nucleotide 2011 or the DNA sequence of FIG. 4 from nucleotide 120 to nucleotide 1742.

4. A DNA module according to claim 1 or 2 wherein said acyloxyacyl hydrolase comprises the amino acid sequence of FIG. 1 from Leucine, number 35 to Histidine, number 575; the amino acid sequence of FIG. 2 from Leucine, number 35 to Histidine, number 575; the amino acid sequence of FIG. 3 from Leucine, number 35 to Histidine, number 575 or the amino acid sequence of FIG. 4 from Leucine, number 35 to Histidine, number 575.

5. A DNA molecule according to claim 1 or 2 wherein said DNA construct further encodes between the small and large subunits the amino acid construct $(R_1)_n$—$R_2$—$R_3$, wherein $R_1$, $R_2$ and $R_3$ are Lys or Arg and n=0, 1, 2, 3, or 4.

6. An isolated DNA molecule according to claims 1 or 2 encoding the small subunit of acyloxyacyl hydrolase.

7. An isolated DNA molecule according to claim 6 wherein said DNA molecule is a cDNA molecule.

8. A DNA molecule according to claim 6 wherein said DNA molecule comprises a DNA molecule of FIG. 1 from nucleotide 354 to nucleotide 713, the DNA sequence of FIG. 2 from nucleotide 354 to nucleotide 713, the DNA sequence of FIG. 3 from nucleotide 389 to nucleotide 748 or the DNA sequence of FIG. 4 from nucleotide 120 to nucleotide 479.

9. A DNA molecule according to claim 6 wherein said small subunit of acyloxyacyl hydrolase comprises the amino acid sequence of FIG. 1 from Leucine, number 35, to Arginine, number 154; the amino acid sequence of FIG. 2 from Leucine, number 35, to Arginine, number 154; the amino acid sequence of FIG. 3 from Leucine, number 35, to Arginine, number 154 or the amino acid sequence of FIG. 4 from Leucine, number 35, to Arginine, number 154.

10. An isolated DNA molecule according to claims 1 or 2 encoding the large subunit of acyloxyacyl hydrolase.

11. An isolated DNA molecule according to claim 10 wherein said DNA molecule is a cDNA molecule.

12. A DNA molecule according to claim 10 wherein said DNA molecule comprises a DNA molecule encoding the DNA sequence of FIG. 1 from nucleotide 720 to nucleotide 1976, the DNA sequence of FIG. 2 from nucleotide 720 to nucleotide 1976, the DNA sequence of FIG. 3 from nucleotide 755 to nucleotide 2011 or the DNA sequence of FIG. 4 from nucleotide 486 to nucleotide 1742.

13. A DNA molecule according to claim 10 wherein said large subunit of acyloxyacyl hydrolase comprises the amino acid sequence of FIG. 1 from Serine, number 157, to Histidine, number 575; the amino acid sequence of FIG. 2 from Serine, number 157, to Histidine number 575; the amino acid sequence of FIG. 3 from Serine, number 157, to Histidine, number 575 or the amino acid sequence of FIG. 4 from Serine, number 157, to Histidine, number 575.

14. A DNA construct comprising the following operably linked elements:
   a transcriptional promoter;
   a DNA sequence encoding acyloxyacyl hydrolase wherein said DNA sequence encodes a small subunit and a large subunit; and
   a transcriptional terminator.

15. A DNA construct according to claim 14 wherein said DNA construct further comprises at least one secretory signal sequence operably linked to said DNA sequence encoding acyloxyacyl hydrolase.

16. A DNA construct according to claim 15 wherein said secretory signal sequence comprises the acyloxyacyl hydrolase secretory signal sequence, the tissue plasminogen activator secretory signal sequence, the α-2 plasmin inhibitor secretory signal sequence, the Sacharomyces cerevisiae BAR1 secretory signal sequence or the Saccaroymes cerevisiae MFα1 secretory signal sequence.

17. A DNA construct according to claim 16 wherein said DNA construct further comprises a DNA sequence encoding the C-terminal domain of the Saccaromyces cerevisiae BAR1 gene operably linked to said DNA sequence.

18. A DNA construct according to claim 15 wherein said secretory signal sequence encodes the amino acid sequence Met-Glu-Ser-Pro-Trp-Lys-Ile-Leu-Thr-Val-Ala-Pro-Leu-Phe-Leu-Leu-Leu-Ser-Pro-Gly-Ala-Trp-Ala-Ser-Pro-Ala-Asn-Asp-Asp-Gln-Ser-Arg-Pro-Ser or Met-Glu-Ser-Pro-Trp-Lys-Ile-Leu-Thr-Val-Ala-Pro-Leu-Phe-Leu-Leu-Leu-Ser-Pro-Gly-Ala-Trp-Ala.

19. A DNA construct according to claim 14 wherein said DNA sequence further encodes between said small and large subunits the amino acid sequence $(R_1)_n$—$R_2$—$R_3$, wherein $R_1$, $R_2$ and $R_3$ are Lys or Arg and n=0, 1, 2 or 3.

20. A DNA construct according to claim 14 wherein said DNA sequence comprises the DNA sequence of FIG. 1 from nucleotide 354 to nucleotide 1976, the DNA sequence of FIG. 2 from nucleotide 354 to nucleotide 1976, the DNA sequence of FIG. 3 from nucleotide 389 to nucleotide 2011 or the DNA sequence of FIG. 4 from nucleotide 120 to nucleotide 1742.

21. A DNA construct according to claim 14 wherein said acyloxyacyl hydrolase comprises the amino acid sequence of FIG. 1 from Leucine, number 35 to Histidine, number 575; the amino acid sequence of FIG. 2 from Leucine, number 35 to Histidine, number 575; the amino acid sequence of FIG. 3 from Leucine, number 35 to Histidine, number 575 or the amino acid sequence of FIG. 4 from Leucine, number 35 to Histidine, number 575.

22. A DNA construct comprising the following operably linked elements:
a transcriptional promoter;
a DNA sequence encoding the small subunit of acyloxyacyl hydrolase; and
a transcriptional terminator.

23. A DNA construct according to claim 22 wherein said DNA construct further comprises at least one secretory signal sequence operably linked to said DNA sequence encoding the small subunit of acyloxyacyl hydrolase.

24. A DNA construct according to claim 23 wherein said secretory signal sequence comprises the acyloxyacyl hydrolase secretory signal sequence, the tissue plasminogen activator secretory signal sequence, the α-2 plasmin inhibitor secretory signal sequence, the *Saccharomyces cerevisiae* BAR1 secretory signal sequence or the *Saccharomyces crevisiae* MFα1 secretory signal sequence.

25. A DNA construct according to claim 24 wherein said DNA construct further comprises a DNA sequence encoding the C-terminal domain of the *Saccharomyces cerevisiae* BAR1 gene operably linked to said DNA sequence.

26. A DNA construct according to claim 23 wherein said secretory signal sequence encodes the amino acid sequence Met-Glu-Ser-Pro-Trp-Lys-Ile-Leu-Thr-Val-Ala-Pro-Leu-Phe-Leu-Leu-Leu-Ser-Pro-Gly-Ala-Trp-Ala-Ser-Pro-Ala-Asn-Asp-Asp-Gln-Ser-Arg-Pro-Ser
or Met-Glu-Ser-Pro-Trp-Lys-Ile-Leu-Thr-Val-Ala-Pro-Leu-Phe-Leu-Leu-Leu-Ser-Pro-Gly-Ala-Trp-Ala.

27. A DNA construct according to claim 22 wherein said DNA sequence comprises the DNA sequence of FIG. 1 from nucleotide 354 to nucleotide 713, the DNA sequence of FIG. 2 from nucleotide 354 to nucleotide 713, the DNA sequence of FIG. 3 from nucleotide 389 to nucleotide 748 or the DNA sequence of FIG. 4 from nucleotide 120 to nucleotide 479.

28. A DNA construct according to claim 22 wherein said small subunit of acyloxyacyl hydrolase comprises the amino acid sequence of FIG. 1 from Leucine, number 35, to Arginine, number 154; the amino acid sequence of FIG. 2 from Leucine, number 35, to Arginine number 154; the amino acid sequence of FIG. 3 from Leucine, number 35, to Arginine, number 154 or the amino acid sequence of FIG. 4 from Leucine, number 35, to Arginine, number 154.

29. A DNA construct comprising the following operably linked elements:
a transcriptional promoter;
a DNA sequence encoding the large subunit of acyloxyacyl hydrolase; and
a transcriptional terminator.

30. A DNA construct according to claim 29 wherein said DNA construct further comprises at least one secretory signal sequence operably linked to said DNA sequence encoding the large subunit of acyloxyacyl hydrolase.

31. A DNA construct according to claim 30 wherein said secretory signal sequence comprises the acyloxyacyl hydrolase secretory signal sequence, the tissue plasminogen activator secretory signal sequence, the α-2 plasmin inhibitor secretory signal sequence, the *Saccharomyces cerevsoae* BAR1 secretory signal sequence or the *Saccharomyces cerevisiae* MFα1 secretory signal sequence.

32. A DNA construct according to claim 31 wherein said DNA construct further comprises a DNA sequence encoding the C-terminal domain of the *Saccharomyces cerevisiae* BAR1 gene operably linked to said DNA sequence.

33. A DNA construct according to claim 30 wherein said secretory signal sequence encodes the amino acid sequence Met-Glu-Ser-Pro-Trp-Lys-Ile-Leu-Thr-Val-Ala-Pro-Leu-Phe-Leu-Leu-Leu-Ser-Pro-Gly-Ala-Trp-Ala-Ser-Pro-Ala-Asn-Asp-Asp-Gln-Ser-Arg-Pro-Ser
or Met-Glu-Ser-Pro-Trp-Lys-Ile-Leu-Thr-Val-Ala-Pro-Leu-Phe-Leu-Leu-Leu-Ser-Pro-Gly-Ala-Trp-Ala.

34. A DNA construct according to claim 29 wherein said DNA sequence comprises the DNA sequence of FIG. 1 from nucleotide 720 to nucleotide 1976, the DNA sequence of FIG. 2 from nucleotide 720 to nucleotide 1976, the DNA sequence of FIG. 3 from nucleotide 755 to nucleotide 2011 or the DNA sequence of FIG. 4 from nucleotide 486 to nucleotide 1742.

35. A DNA construct according to claim 29 wherein said large subunit of acyloxyacyl hydrolase comprises the amino acid sequence of FIG. 1 from Serine, number 157, to Histidine, number 575; the amino acid sequence of FIG. 2 from Serine, number 157, to Histidine number 575; the amino acid sequence of FIG. 3 from Serine, number 157, to Histidine, number 575 or the amino acid sequence of FIG. 4 from Serine, number 157, to Histidine, number 575.

36. A cultured eukaryotic host cell containing a DNA construct comprising the following operably linked elements:
a transcriptional promoter;
an isolated DNA sequence encoding acyloxyacyl hydrolase wherein said DNA sequence encodes a small subunit and a large subunit; and
a transcriptional terminator.

37. A eukaryotic cell according to claim 36 wherein the DNA construct further comprises a secretory signal sequence operably linked to said DNA sequence encoding acyloxyacyl hydrolase.

38. A eukaryotic cell according to claim 37 wherein said secretory signal sequence comprises the acyloxyacyl hydrolase secretory signal sequence, the tissue plasminogen activator secretory signal sequence, the α-2 plasmin inhibitor secretory signal sequence, the *Saccharomyces cerevisiae* BAR1 secretory signal sequence or the *Saccharomyces cerevisiae* MFα1 secretory signal sequence.

39. A eukaryotic cell according to claim 38 wherein said DNA construct further comprises a DNA sequence encoding the C-terminal domain of the *Saccharomyces cerevisiae* BAR1 gene operably linked to said DNA sequence.

40. A eukaryotic cell according to claim 36 wherein said secretory signal sequence encodes the amino acid sequence Met-Glu-Ser-Pro-Trp-Lys-Ile-Leu-Thr-Val-Ala-Pro-Leu-Phe-Leu-Leu-Leu-Ser-Pro-Gly-Ala-Trp-Ala-Ser-Pro-Ala-Asn-Asp-Asp-Gln-Ser-Arg-Pro-Ser or Met-Glu-Ser-Pro-Trp-Lys-Ile-Leu-Thr-Val-Ala-Pro-Phe-Leu-Leu-Leu-Ser-Pro-Gly-Ala-Trp-Ala.

41. A eukaryotic cell according to claim 36 wherein said DNA sequence comprises the DNA sequence of FIG. 1 from nucleotide 354 to nucleotide 1976, the DNA sequence of FIG. 2 from nucleotide 354 to nucleotide 1976, the DNA sequence of FIG. 3 from nucleotide 389 to nucleotide 2011 or the DNA sequence of FIG. 4 from nucleotide 120 to nucleotide 1742.

42. A eukaryotic cell according to claim 36 wherein said acyloxyacyl hydrolase comprises the amino acid sequence of FIG. 1 from Leucine, number 35, to Histidine, number 575; the amino acid sequence of FIG. 2 from Leucine, number 35, to Histidine, number 575; the amino acid sequence of FIG. 3 from Leucine, number 35, to Histidine, number 575 or the amino acid sequence of FIG. 4 from Leucine, number 35, to Histidine, number 575.

43. A eukaryotic cell according to claim 36 wherein said cell is a cultured mammalian cell or a yeast cell.

44. A eukaryotic cell according to claim 36 wherein said DNA sequence further encodes the amino acid sequence $(R_1)_n$—$R_2$—$R_3$, wherein $R_1$, $R_2$ and $R_3$ are Lys or Arg and n=0, 1, 2 or 3, between said small and large subunits.

45. A eukaryotic host cell transformed or transfected with a first DNA construct containing the information necessary to direct the expression of the large subunit of acyloxyacyl hydrolase and a second DNA construct containing the information necessary to direct the expression of the small subunit of acyloxyacyl hydrolase.

46. A eukaryotic cell according to claim 45 wherein said cell is a cultured mammalian cell or a yeast cell.

47. A eukaryotic cell containing a first DNA construct containing the information necessary to direct the secretion of the large subunit of acyloxyacyl hydrolase and a second DNA construct containing the information necessary to direct the secretion of the small subunit of acyloxyacyl hydrolase.

48. A eukaryotic cell according to claim 47 wherein said cell is a cultured mammalian cell or a yeast cell.

49. A method for producing acyloxyacyl hydrolase comprising the steps of:
(a) growing cultured eukaryotic cells transformed or transfected with a DNA construct containing the information necessary to direct the expression of acyloxyacyl hydrolase; and
(b) isolating the acyloxyacyl hydrolase from said cells.

50. A method according to claim 49 wherein said eukaryotic cells are cultured mammalian cells or yeast cells.

51. A method for producing acyloxyacyl hydrolase comprising the steps of:
(a) growing, in a suitable medium, eukaryotic cells transformed or transfected with a DNA construct containing the information necessary to direct the secretion of acyloxyacyl hydrolase; and
(b) isolating the acyloxyacyl hydrolase from said cells or from said medium.

52. A method according to claim 51 wherein said eukaryotic cells are cultured mammalian cells or yeast cells.

53. A method for producing acyloxyacyl hydrolase comprising the steps of:
(a) growing, in a suitable medium, eukaryotic cells transformed or transfected with a first DNA construct containing the information necessary to direct the expression of the large subunit of acyloxyacyl hydrolase and a second DNA construct containing the information necessary to direct the expression of the small subunit of acyloxyacyl hydrolase; and
(b) isolating the acyloxyacyl hydrolase from the cells or from said medium.

54. A method according to claim 53 wherein said eukaryotic cells are cultured mammalian cells or yeast cells.

55. A method for producing acyloxyacyl hydrolase comprising the steps of:
(a) growing, in a suitable medium eukaryotic cells transformed or transfected with a first DNA construct containing the information necessary to direct the secretion of the large subunit of acyloxyacyl hydrolase and a second DNA construct containing the information necessary to direct the secretion of the small subunit of acyloxyacyl hydrolase; and
(b) isolating the acyloxyacyl hydrolase from the cells or from said medium.

56. A method according to claim 55 wherein said eukaryotic cells are cultured mammalian cells or yeast cells.

* * * * *